(12) United States Patent
Diamond et al.

(10) Patent No.: US 7,172,572 B2
(45) Date of Patent: *Feb. 6, 2007

(54) MANIFOLD SYSTEM FOR A MEDICAL DEVICE

(75) Inventors: Scott A. Diamond, Fort Edward, NY (US); Colin P. Hart, Queensbury, NY (US); James Mitchell, Schaghticoke, NY (US); Thomas Deyette, Jr., Hudson Falls, NY (US); Richard M. Garlapow, Grand Island, NY (US); Mark H. Van Diver, Argyle, NY (US); William A. Wetherbee, Queensbury, NY (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 350 days.

This patent is subject to a terminal disclaimer.

(21) Appl. No.: 10/375,658

(22) Filed: Feb. 26, 2003

(65) Prior Publication Data

US 2003/0181850 A1    Sep. 25, 2003

Related U.S. Application Data

(63) Continuation-in-part of application No. 10/278,663, filed on Oct. 23, 2002, now Pat. No. 6,976,974, and a continuation-in-part of application No. 10/263,018, filed on Oct. 2, 2002, now Pat. No. 6,918,893.

(60) Provisional application No. 60/326,941, filed on Oct. 4, 2001.

(51) Int. Cl.
*A61M 1/00*    (2006.01)
*A61M 5/00*    (2006.01)
*F16K 11/074*  (2006.01)
*F16K 11/07*   (2006.01)

(52) U.S. Cl. .................. 604/32; 604/248; 137/625.21; 137/625.41

(58) Field of Classification Search .............. 604/30, 604/325, 80, 181, 187, 191, 246, 248, 257, 604/258, 284, 533, 534, 535, 537, 538, 539; 137/625.21, 625.22, 625.23, 625.24, 625.4, 137/625.41, 625.42, 625.46, 602
See application file for complete search history.

(56) References Cited

U.S. PATENT DOCUMENTS

| | | | |
|---|---|---|---|
| 3,157,201 A | * | 11/1964 | Littmann ............... 137/625.47 |
| 3,384,372 A | | 5/1968 | Dickens |
| 3,774,604 A | | 11/1973 | Danielsson |
| 3,834,372 A | | 9/1974 | Turney |
| 3,939,832 A | | 2/1976 | Miller |

(Continued)

FOREIGN PATENT DOCUMENTS

AU           458 487 B1     2/1975

(Continued)

OTHER PUBLICATIONS

U.S. Appl. No. 10/262,924 to Eric Houde, filed Oct. 2, 2002.

*Primary Examiner*—Kevin C. Sirmons
*Assistant Examiner*—Mark K Han
(74) *Attorney, Agent, or Firm*—Crompton, Seager & Tufte, LLC

(57) ABSTRACT

A number of devices are illustrated for providing a manifold that can simply and selectively couple a number of different therapeutic and diagnostic elements to a catheter or other medical device. Some examples include devices having sliding actuators, rotary actuators, button actuators, or combinations thereof, for easily changing the valve scheme and fluid pathways within a manifold.

25 Claims, 27 Drawing Sheets

U.S. PATENT DOCUMENTS

| | | |
|---|---|---|
| 4,204,535 A | 5/1980 | Pohlmann |
| 4,342,315 A | 8/1982 | Jackson |
| 4,430,074 A | 2/1984 | Mooring |
| 4,435,171 A | 3/1984 | Goldberg et al. |
| 4,447,230 A | 5/1984 | Gula et al. |
| 4,447,236 A | 5/1984 | Quinn |
| 4,512,764 A | 4/1985 | Wunsch |
| 4,559,036 A | 12/1985 | Wunsch |
| 4,604,090 A | 8/1986 | Reinicke |
| 4,604,093 A | 8/1986 | Brown et al. |
| 4,620,846 A | 11/1986 | Goldberg et al. |
| 4,621,647 A | 11/1986 | Loveland |
| 4,648,870 A | 3/1987 | Goldberg et al. |
| 4,653,539 A | 3/1987 | Bell |
| 4,669,465 A | 6/1987 | Moore et al. |
| 4,699,615 A | 10/1987 | Fischell et al. |
| 4,705,501 A | 11/1987 | Wigness et al. |
| 4,769,017 A | 9/1988 | Fath et al. |
| 4,789,000 A | 12/1988 | Aslanian |
| 4,790,193 A | 12/1988 | Moriuchi et al. |
| 4,813,927 A | 3/1989 | Morris et al. |
| 4,819,653 A | 4/1989 | Marks |
| 4,846,806 A | 7/1989 | Wigness et al. |
| 4,871,353 A | 10/1989 | Thomsen |
| 4,908,018 A | 3/1990 | Thomsen |
| 4,915,688 A | 4/1990 | Bischof et al. |
| 4,927,411 A | 5/1990 | Pastrone et al. |
| 4,936,542 A | 6/1990 | Beard |
| 5,020,562 A | 6/1991 | Richmond et al. |
| 5,074,334 A | 12/1991 | Onodera |
| 5,084,031 A | 1/1992 | Todd et al. |
| 5,104,387 A | 4/1992 | Pokorney et al. |
| 5,112,301 A | 5/1992 | Fenton, Jr. et al. |
| 5,134,079 A | 7/1992 | Cusack et al. |
| 5,135,502 A | 8/1992 | Koenig, Jr. et al. |
| 5,148,811 A | 9/1992 | Messinger |
| 5,163,902 A | 11/1992 | Lynn et al. |
| 5,163,904 A | 11/1992 | Lampropoulos et al. |
| 5,168,901 A | 12/1992 | Marks |
| 5,171,216 A | 12/1992 | Dasse et al. |
| 5,171,230 A | 12/1992 | Eland et al. |
| 5,190,525 A | 3/1993 | Oswald et al. |
| 5,217,432 A | 6/1993 | Rudzena et al. |
| 5,232,024 A | 8/1993 | Williams |
| 5,236,417 A | 8/1993 | Wallis |
| 5,288,290 A | 2/1994 | Brody |
| 5,290,263 A | 3/1994 | Wigness et al. |
| 5,324,274 A | 6/1994 | Martin |
| 5,328,463 A | 7/1994 | Barton et al. |
| 5,333,607 A | 8/1994 | Kee et al. |
| 5,334,170 A | 8/1994 | Moroski |
| 5,354,284 A | 10/1994 | Haber et al. |
| 5,356,375 A | 10/1994 | Higley |
| 5,357,946 A | 10/1994 | Kee et al. |
| 5,378,229 A | 1/1995 | Layer et al. |
| 5,380,665 A | 1/1995 | Cusack et al. |
| 5,399,172 A | 3/1995 | Martin et al. |
| 5,407,424 A | 4/1995 | LaFontaine et al. |
| 5,423,751 A | 6/1995 | Harrison et al. |
| 5,431,185 A | 7/1995 | Shannon et al. |
| 5,443,450 A | 8/1995 | Kratoska et al. |
| 5,445,141 A | 8/1995 | Kee et al. |
| 5,445,616 A | 8/1995 | Kratoska et al. |
| 5,454,792 A | 10/1995 | Tennican et al. |
| 5,466,227 A | 11/1995 | Kessenich |
| 5,485,831 A | 1/1996 | Holdsworth et al. |
| 5,496,273 A | 3/1996 | Pastrone et al. |
| 5,501,674 A | 3/1996 | Trombley, III et al. |
| 5,515,851 A | 5/1996 | Goldstein |
| 5,520,666 A | 5/1996 | Choudhury et al. |
| 5,533,978 A | 7/1996 | Teirstein |
| 5,545,141 A | 8/1996 | Eld |
| 5,551,849 A | 9/1996 | Christiansen |
| 5,562,614 A | 10/1996 | O'Donnell |
| 5,569,208 A | 10/1996 | Woelpper et al. |
| 5,575,767 A | 11/1996 | Stevens |
| 5,575,779 A | 11/1996 | Barry |
| 5,578,059 A | 11/1996 | Patzer |
| 5,593,385 A | 1/1997 | Harrison et al. |
| 5,601,651 A | 2/1997 | Watabe |
| 5,618,268 A | 4/1997 | Raines et al. |
| 5,628,306 A | 5/1997 | Kee |
| 5,640,995 A | 6/1997 | Packard et al. |
| 5,665,074 A | 9/1997 | Kelly |
| 5,681,339 A | 10/1997 | McEwen et al. |
| 5,697,899 A | 12/1997 | Hillman et al. |
| 5,697,904 A | 12/1997 | Raines et al. |
| 5,730,731 A | 3/1998 | Mollenauer et al. |
| 5,738,662 A | 4/1998 | Shannon et al. |
| 5,743,872 A | 4/1998 | Kelly |
| 5,779,666 A | 7/1998 | Teirstein |
| 5,788,215 A | 8/1998 | Ryan |
| 5,800,383 A | 9/1998 | Chandler et al. |
| 5,800,397 A | 9/1998 | Wilson et al. |
| 5,800,408 A | 9/1998 | Strauss et al. |
| 5,806,519 A | 9/1998 | Evans, III et al. |
| 5,827,219 A | 10/1998 | Uber, III et al. |
| 5,830,180 A | 11/1998 | Chandler et al. |
| 5,840,026 A | 11/1998 | Uber, III et al. |
| 5,882,348 A | 3/1999 | Winterton et al. |
| 5,911,708 A | 6/1999 | Teirstein |
| 5,934,888 A | 8/1999 | Marka et al. |
| 6,001,112 A | 12/1999 | Taylor |
| 6,017,318 A | 1/2000 | Gauthier et al. |
| 6,063,052 A | 5/2000 | Uber, III et al. |
| 6,083,205 A | 7/2000 | Bourne et al. |
| 6,099,502 A | 8/2000 | Duchon et al. |
| 6,099,511 A | 8/2000 | Devos et al. |
| 6,110,144 A | 8/2000 | Choh et al. |
| 6,117,102 A | 9/2000 | Schwartz et al. |
| 6,135,153 A | 10/2000 | Cleland, Sr., deceased et al. |
| 6,146,360 A | 11/2000 | Rogers et al. |
| 6,176,843 B1 | 1/2001 | DiCaprio et al. |
| 6,221,045 B1 | 4/2001 | Duchon et al. |
| 6,238,372 B1 | 5/2001 | Zinger et al. |
| 6,242,472 B1 | 6/2001 | Sekins et al. |
| 6,315,762 B1 | 11/2001 | Recinella et al. |
| 6,325,777 B1 | 12/2001 | Zadno-Azizi et al. |
| 6,325,778 B1 | 12/2001 | Zadno-Azizi et al. |
| 6,344,030 B1 | 2/2002 | Duchon et al. |
| 6,355,014 B1 | 3/2002 | Zadno-Azizi et al. |
| 6,361,528 B1 | 3/2002 | Wilson et al. |
| 6,371,942 B1 | 4/2002 | Schwartz et al. |
| 6,416,496 B1 | 7/2002 | Rogers et al. |
| 6,447,481 B1 | 9/2002 | Duchon et al. |
| 6,454,779 B1 | 9/2002 | Taylor |
| 6,537,268 B1 | 3/2003 | Gibson et al. |
| 6,544,232 B1 | 4/2003 | McDaniel |
| 2001/0044618 A1 | 11/2001 | Recinella et al. |
| 2002/0022807 A1 | 2/2002 | Duchon et al. |
| 2002/0038105 A1 | 3/2002 | Schwartz et al. |
| 2002/0095117 A1 | 7/2002 | Wilson et al. |
| 2002/0143294 A1 | 10/2002 | Duchon et al. |
| 2002/0151854 A1 | 10/2002 | Duchon et al. |

FOREIGN PATENT DOCUMENTS

| | | |
|---|---|---|
| EP | 1 091 164 A1 | 4/2001 |
| FR | 2 804 609 A1 | 8/2001 |
| WO | WO 97/18632 A1 | 12/1991 |
| WO | WO 03/039646 A1 | 5/2003 |

* cited by examiner

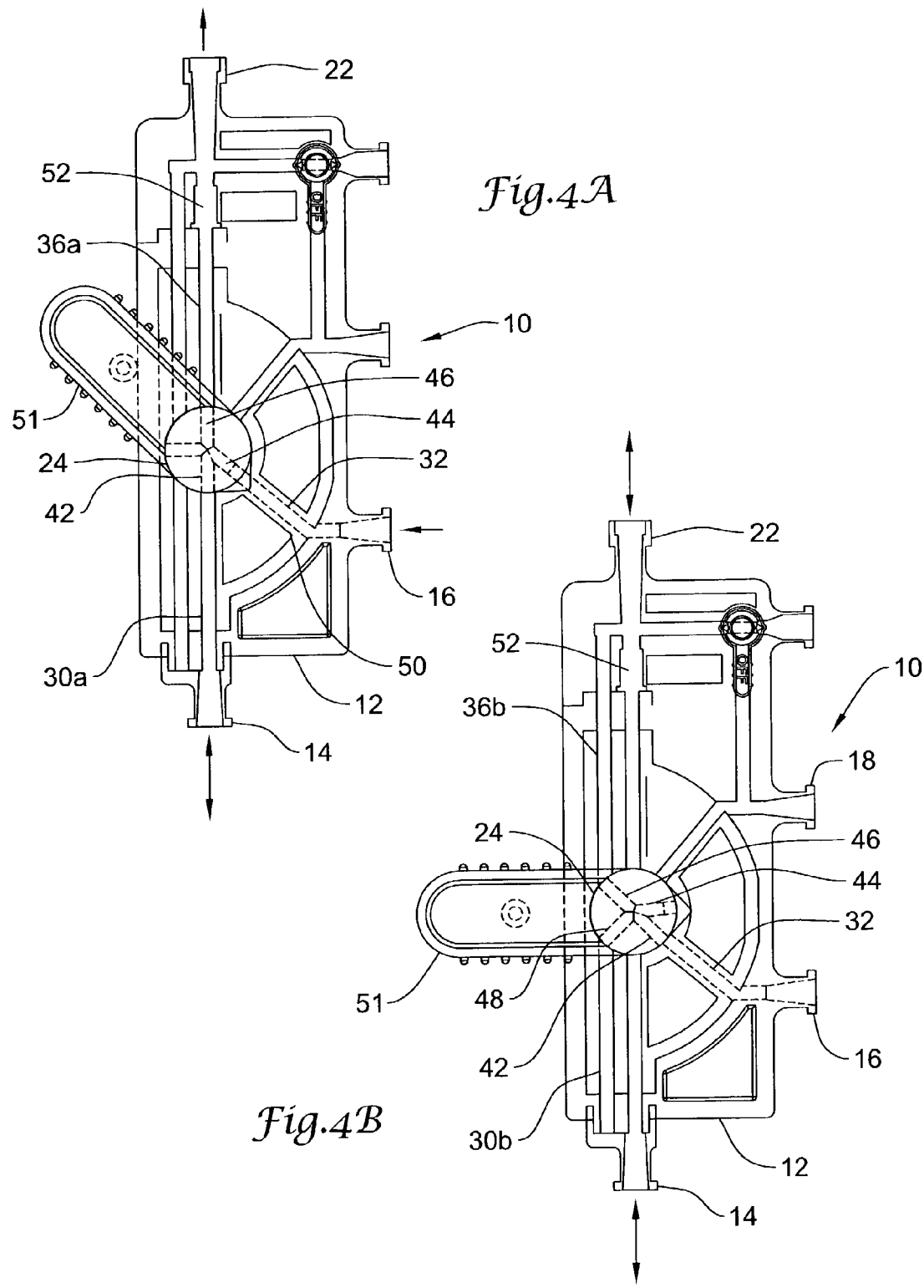

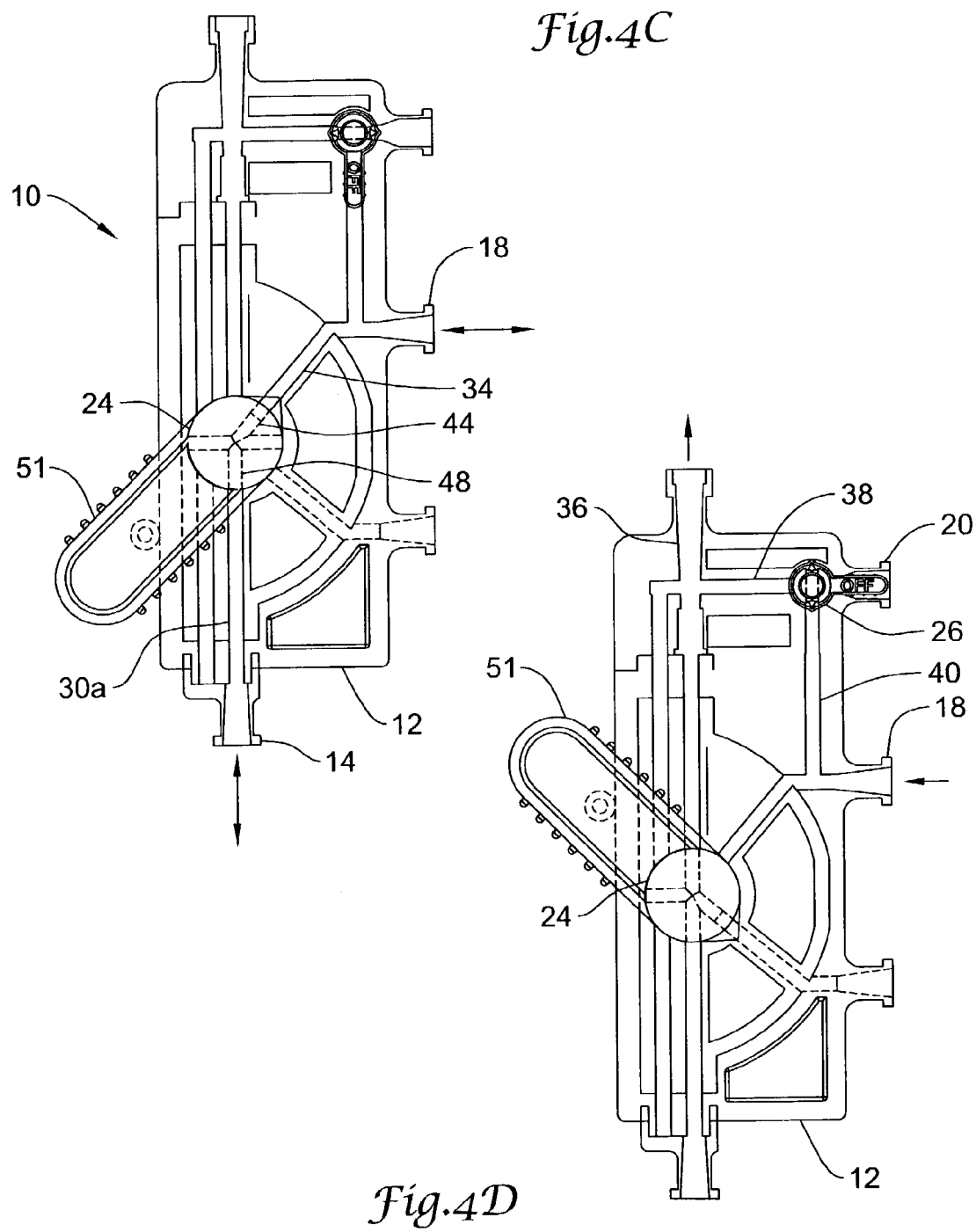

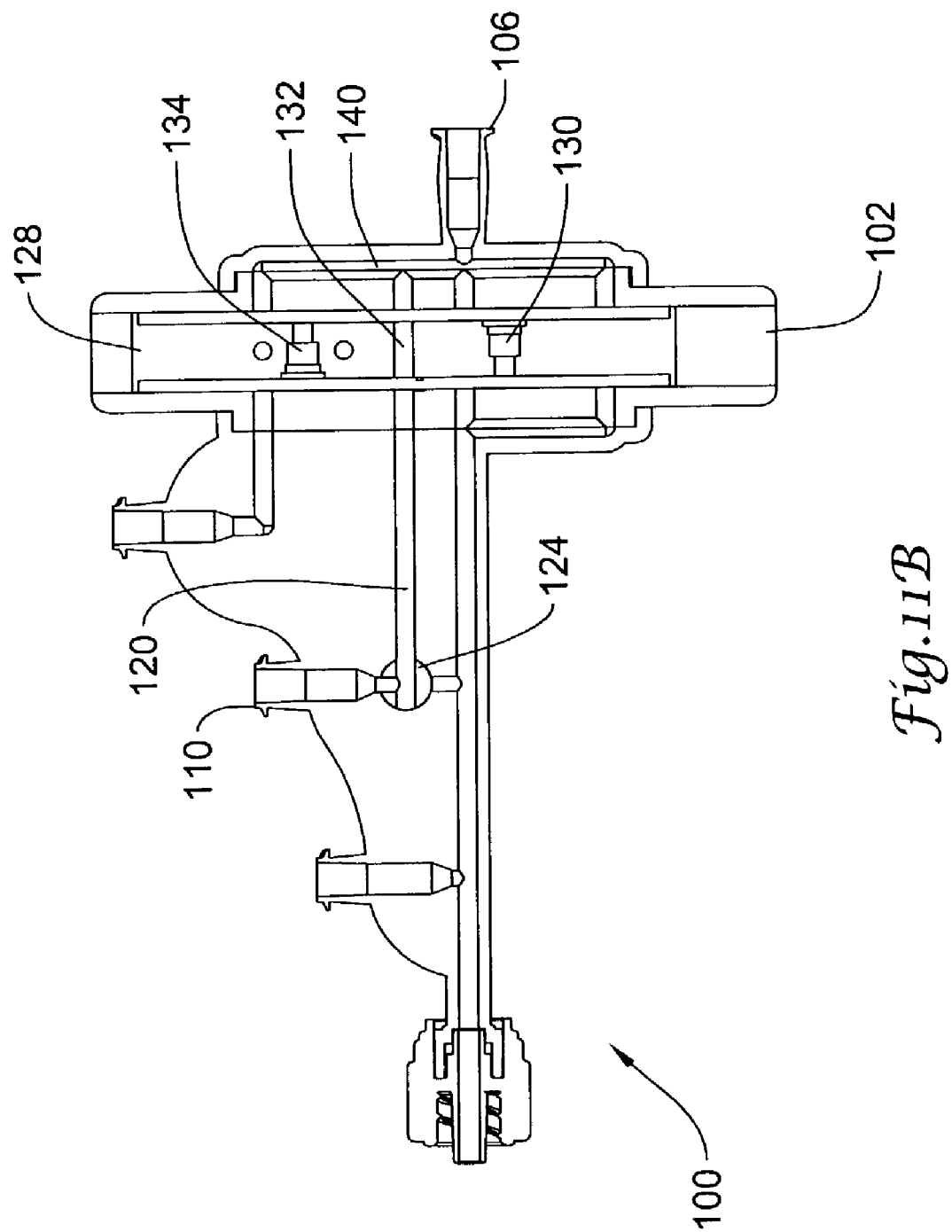

MANIFOLD SYSTEM FOR A MEDICAL DEVICE

CROSS REFERENCE TO RELATED APPLICATIONS

This application is a continuation-in-part of U.S. patent application Ser. No. 10/263,018, filed Oct. 2, 2002 now U.S. Pat. No. 6,918,893; which claims benefit of U.S. Provisional Application No. 60/326,941, filed Oct. 4, 2001, the entire disclosure of which is hereby incorporated by reference. This application is also a continuation-in-part of U.S. patent application Ser. No. 10/278,663, filed Oct. 23, 2002, now U.S. Pat. No. 6,976,974 the entire disclosure of which is hereby incorporated by reference.

FIELD OF THE INVENTION

The invention is related to the area of medical devices. More particularly, the invention is related to manifolds for coupling fluid and pressure/suction sources to a medical device such as a catheter or cannula.

BACKGROUND OF THE INVENTION

Manifolds for use with catheters and other medical devices are used for several different functions. Some such manifolds couple more than one fluid source to a catheter, as well as a source of pressure and suction such as a syringe. Presently, manifolds coupling several fluid sources and/or pressure or suction sources to a medical device may include a number of individual valves that must be separately and repeatedly manipulated during a procedure. The process of using such manifolds complicates the operations performed, extends the time needed for an operation, and can lead to mistakes.

SUMMARY OF THE INVENTION

The present invention, in an illustrative embodiment, provides a manifold device which simplifies the control over fluid devices and pressure or suction sources when coupled to a catheter or other medical device. In one embodiment, a manifold is provided having multiple ports. The ports may include ports for receiving therapeutic or diagnostic substance sources, a saline source, a waste receptacle, and pressure and/or suction devices. The therapeutic or diagnostic substance source may be a source for a contrast medium, a drug, or an antibiotic or other medicine, for example. Other devices or sources may be coupled to the manifold as well, either in addition to or as replacements to those already noted. The saline source and waste receptacle, in some embodiments, may be provided with a single input port which is adapted for coupling to a device including a double check valve mechanism used to prevent fluid from flowing back into the saline supply and substances from escaping the waste receptacle. A medical device port is also provided for coupling to a catheter or other medical device.

A valve member is provided for performing multiple valve functions within the valve member, preferably simultaneously with a change in position. The valve member may be adapted to have several predefined positions or configurations. A first position may couple a contrast medium source port to a pressure/suction device port and a main output line port while closing other ports, the first position being adapted for infusing the contrast medium. The first position may also be used for coupling to other sources of therapeutic or diagnostic solutions. A second position may couple the pressure/suction device port to the saline/waste port, the second position being adapted for flushing the chamber of the manifold and the pressure/suction device. A third position may couple the pressure/suction device port with the medical device port, the third position being adapted for allowing fluid to be drawn through the catheter or other medical device. In some embodiments, a fourth position is provided for the injection of saline where a pressurized saline source is provided, the fourth position coupling a special saline injection port or the saline/waste port to the main output line port, while closing other ports.

In some embodiments, the valve member may be provided as a rotating actuator, a sliding actuator, a pushbutton actuator, or a variety of hybrids and/or combinations of these designs. A number of seals, O-rings, valves, and other elements may also be provided variously to provide a structure for performing the functions of the valve member. Check valves are included in several embodiments for controlling or limiting the direction of fluid flow, for example, to prevent fluid from back flowing to a contrast medium source.

BRIEF DESCRIPTION OF THE DRAWINGS

FIGS. 4A–4D are schematic cross section representations of a flat rotor design illustrative embodiment showing four operational configurations;

FIGS. 11A–11D are schematic cross section representations of the slider design of FIG. 8 showing four operational configurations;

DETAILED DESCRIPTION OF THE SEVERAL EMBODIMENTS

The following detailed description should be read with reference to the drawings. The drawings, which are not necessarily to scale, depict illustrative embodiments and are not intended to limit the scope of the invention.

While the following detailed description is written with reference to a catheter port (e.g., catheter port 22 described in FIG. 1), it should be understood that the term catheter port is used in its most general sense. For example, where a multi-lumen catheter is used, a short coupling piece may couple a "catheter port" to a Luer valve on the proximal end of a Y or other connector placed to allow separate access to the several lumens of a multi–lumen catheter. An introducer sheath or other sheath, cannula, endoscope or any other single or multi-lumen medical device adapted for at least partial insertion into a patient by any vascular or non-vascular route may be coupled directly or indirectly to the present devices via a "catheter port."

Any of the ports described below may include any number of sealing devices or configurations. For example, a dual flexible membrane may be incorporated such that, if a port is not connected to another element, fluid flow out of the port is prevented. Such sealing devices or configurations may be adapted to allow various devices to be inserted therethrough while also providing a fluid seal around an inserted device.

A wide variety of materials may be used in the construction of embodiments such as those disclosed herein. Typical materials may include a polycarbonate for the bodies and housing members, as well as in defining the various bores, with acetal materials used for the various rotating and sliding actuators, though any suitable material including, for example, acrylics, polyolefins, engineering polymers, blends and alloys of any of an array of polymers, as well as self-lubricating polymers may be used. Sealing may be accomplished by the use of an interference fit, though alternative methods may be used including the use of elastomeric seals and o-rings. The various components may be assembled using bonding techniques including solvents, UV cured adhesives; welding techniques including ultrasonic, thermal or spin techniques; or snap fits and/or other mechanical attachment devices. A number of check valves are used in the following exemplary designs, many of which are included to illustrate particular uses and which may be omitted in some embodiments. The various check valves may be accomplished by any suitable structure or technique, including but not limited to umbrella valves, duckbill valves, disk valves, ball check valves, flapper type valves, and the like. Different types of valves may be incorporated at different locations within the same design.

Figure 1:
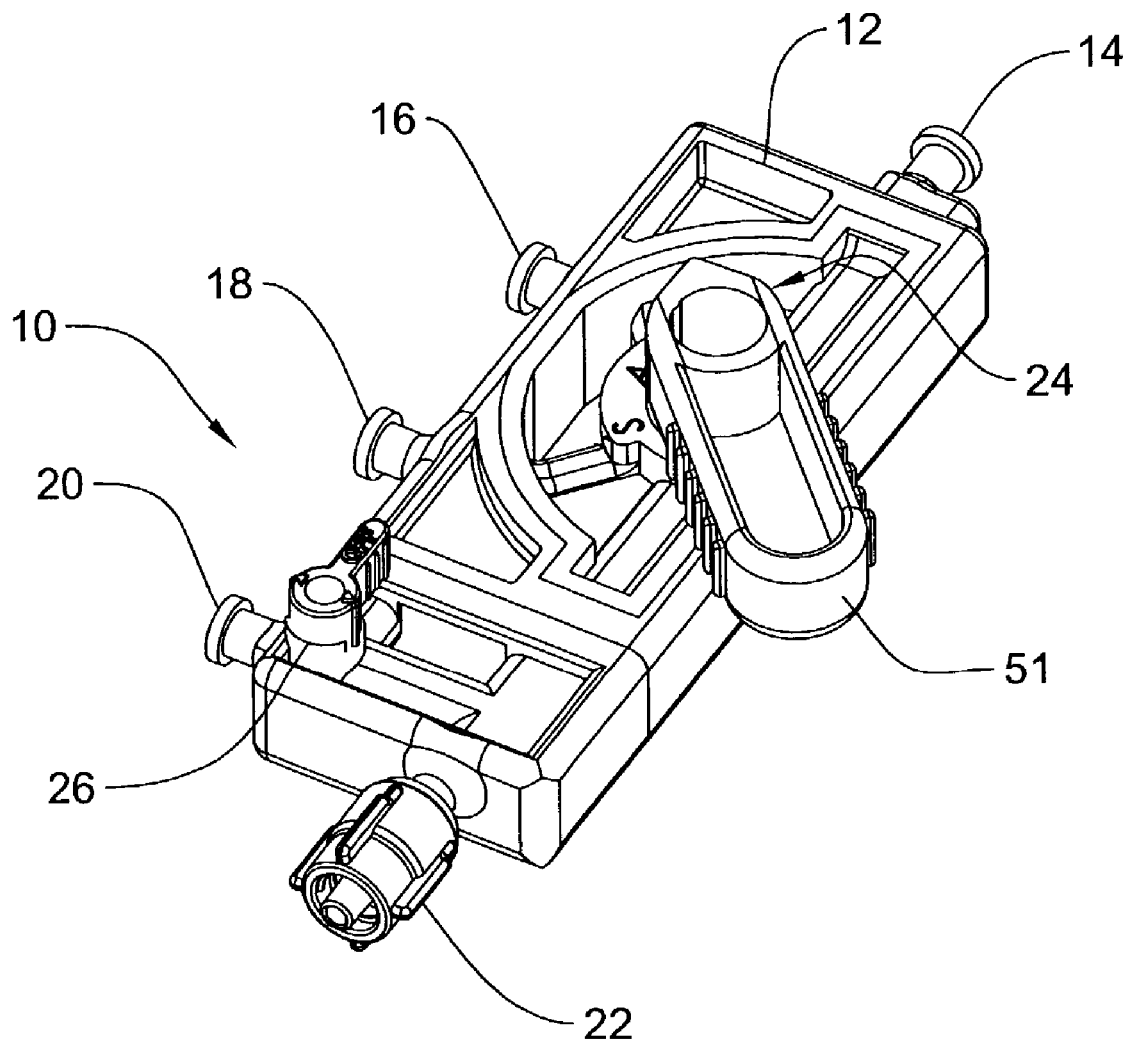
FIG. 1 is a perspective view of a first illustrative embodiment having a rotating actuator in a flat rotor design.

FIG. 1 is a perspective view of a first illustrative embodiment having a rotating actuator in a relatively flat rotor design. The manifold 10 includes a housing 12 having a syringe port 14, a contrast port 16, a saline/waste port 18, an auxiliary port 20 and a catheter port 22. The rotating actuator 24 is held within the housing 12 and, along with several bores (shown in greater detail in FIG. 2) through the housing 12, the rotating actuator 24 provides selective coupling between the various ports 14, 16, 18, 20, 22. These couplings are further explained with reference to FIGS. 2 and 4A–4D.

The auxiliary port 20 may provide a number of functions, including, for example allowing infusion of medication and/or pressure monitoring. The auxiliary port 20 is provided with an inline valve rotor 26, which may be a stopcock and is further explained with reference to FIGS. 2 and 4D. For example, the blood pressure of a patient may be monitored during a procedure by the use of a pressure transducer coupled at the auxiliary port 22, or the pressure inside a catheter may be monitored to prevent over-pressurization which could result in rupture of a shaft or an inflatable membrane. The valve rotor 26 may also be useful as an emergency pressure release location, for example, if a syringe is attached to syringe port 14, pressure is applied, and a locking mechanism on the syringe fails to release properly when desired; for such use the auxiliary port 20 may act as an emergency fluid evacuation port.

Figure 2:
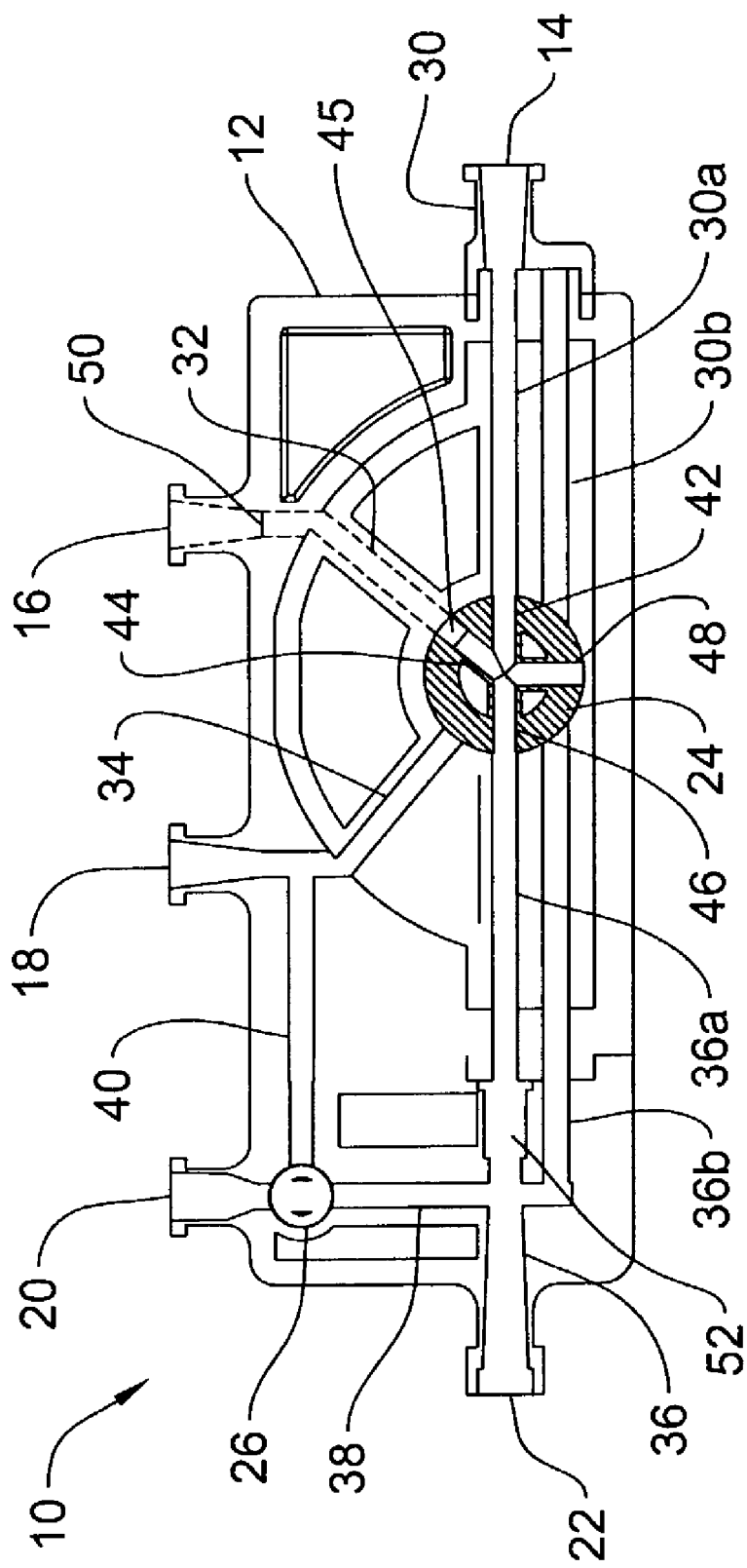
FIG. 2 is a cross sectional view of the housing and rotating actuator of FIG. 1 showing in part the bores and valves used.

FIG. 2 is a cross sectional view of parts from the embodiment of FIG. 1 showing the bores of the housing 12 and rotating actuator 24. The housing 12 includes a branching syringe bore 30, 30a, 30b, a contrast bore 32, a saline/waste bore 34, a branching main outlet bore 36, 36a, 36b, an auxiliary bore 38, and a pressurized saline bore 40. The rotating actuator 24 is illustrated in a first position for injecting contrast into a medical device attached to the catheter port 22. It can be seen that the rotating actuator 24 includes a first bore 42, a second bore 44, a third bore 46 and a fourth bore 48, all of which connect within the rotating actuator 24. In other embodiments, various bores may be isolated from one another as well.

Two optional check valves 50, 52 are also shown, with one check valve 50 disposed to prevent fluid flow back toward the contrast port 16 and the other check valve 52 disposed to prevent fluid flow in from the catheter port 22. When the rotating actuator 24 is in the first position as illustrated in FIG. 2, the first bore 42 couples to a branch 30a of the syringe bore 30, the second bore 44 couples to the contrast bore 32, and the third bore 46 couples to a branch 36a of the main outlet bore 36. When the syringe or other pressure/suction device attached at syringe port 14 is used to apply suction (e.g., the plunger of a syringe is drawn back), one check valve 52 prevents fluid from flowing in from the catheter port 22 while the other check valve 50 allows contrast media to flow in from the contrast port 16. The coupling of the several bores and the rotating actuator creates fluid communication allowing contrast fluid to be drawn into the pressure/suction device (e.g., the barrel of a syringe) attached at the syringe port 14. When pressure is subsequently applied at the syringe port 14, one check valve 50 prevents the contrast fluid from flowing back up to the contrast port 16, while the other check valve 52 allows contrast fluid to be infused to a medical device out through the catheter port 22.

The branches 30a, 30b, 36a, 36b of the syringe bore 30 and the main outlet bore 36 are included to provide additional fluid flow routes through the housing 12. For example, if the rotating actuator 24 were turned counter-clockwise about its axis for about 45 degrees, the third bore 46 would couple to the main outlet branch 36b and the fourth bore 48 would couple to the syringe branch 30b. This different fluid path does not include the check valve 52, and allows for aspiration of fluid from a medical device attached to the catheter port 22 into a pressure/suction device coupled to the syringe port 14.

Alternatively, if the rotating actuator 24 is turned counterclockwise from the first position shown by about 90 degrees, the second bore 44 would couple to the saline bore 34, while the fourth bore 48 couples to syringe branch 30a. This position allows for flushing of the pressure/suction device attached to the syringe port 14 as well as the manifold 10 itself, by allowing saline to be drawn into the manifold 10, through the several bores, and into the pressure/suction device. Once saline is drawn in, the saline may be flushed out via the same route. The manifold 10 is adapted to be connected at saline/waste port 18 to a saline/waste combination device which includes an internal double check valve mechanism, allowing saline to be drawn while also allowing waste to be received and preventing the mixing of the two. If such a device is not desired, separate saline and waste ports may be provided, and each may include a check valve to prevent undesired flow to a saline source or from a waste receptacle. If separate ports are provided, the bores in the housing 12 may be coupled together to achieve a similar effect to that achieved using a saline/waste combination device if so desired.

If desired, a pressurized saline source may be used and coupled via the saline/waste port 18. In such use, the rotor valve 26 may be a three-way stopcock, allowing, in one position, fluid communication between each of the auxiliary port 20, the auxiliary bore 38, and the pressurized saline bore 40 which couples to the saline/waste port 18. In this position, for example, a pressure transducer may be provided on the auxiliary port 20 to monitor fluid infusion pressures, while saline is injected from saline/waste port 18 to a medical device attached at the catheter port 22. A syringe or other device may be coupled to the auxiliary port 20 for infusing a medicine or other substance while pressurized saline is injected via the saline/waste port 18.

Figure 3:
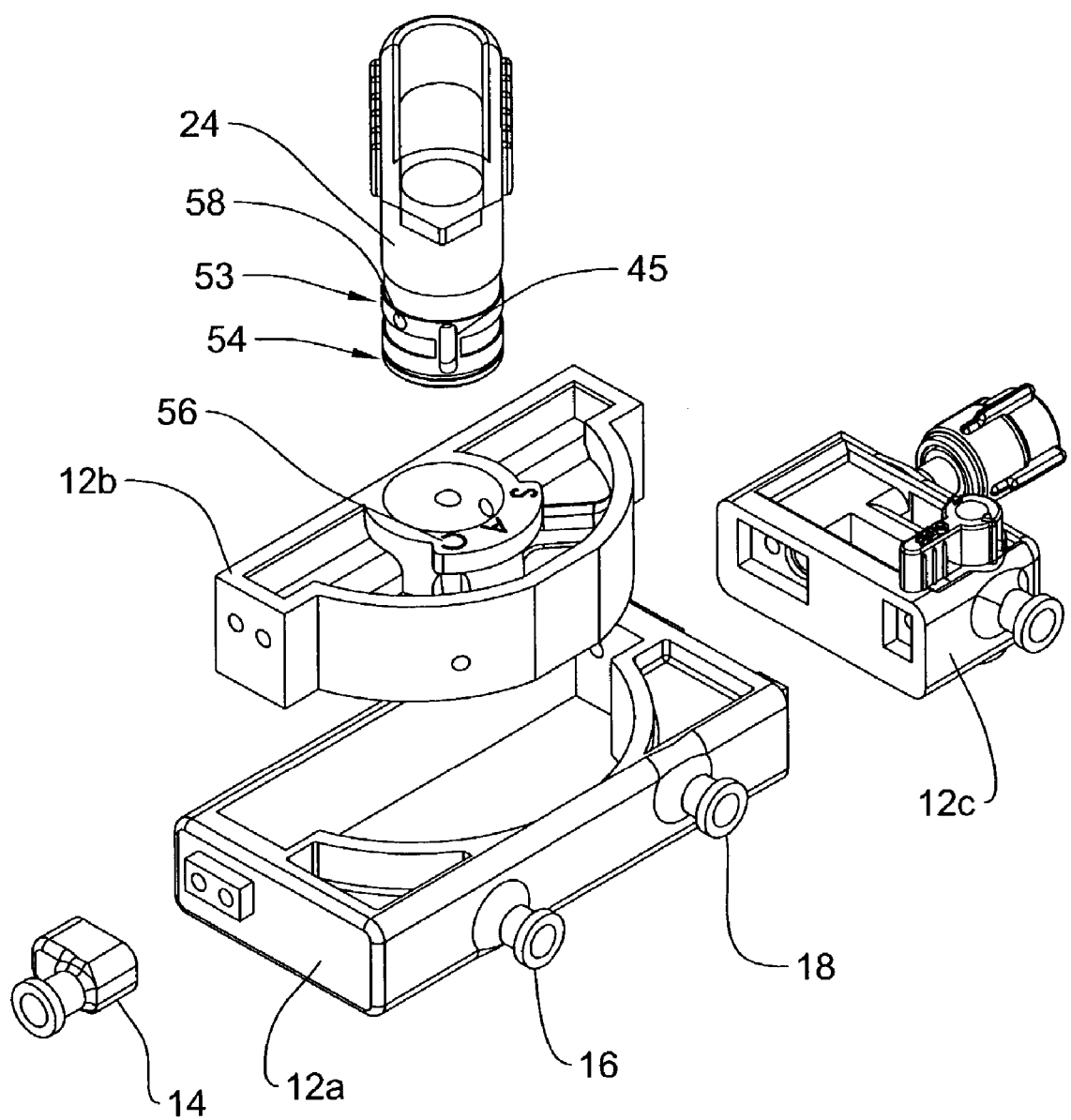
FIG. 3 is an exploded view of the various parts of the illustrative embodiment of FIG. 1.

FIG. 3 is an exploded view of the various parts of the illustrative embodiment of FIG. 1. Particular emphasis is placed on the construction of the housing 12 and the rotating actuator 24. The housing 12, as can be seen, includes an outer housing element 12a, an inner housing element 12b and an output housing element 12c. The outer housing 12a includes locations for coupling of the ports 14, 16, 18 and the output housing 12c. The housing elements 12a, 12b, and 12c can be attached together by any suitable mechanism or manner.

It can be seen that the contrast port 16 is placed on a lower portion of the outer housing element 12a, while the other elements including the syringe port 14 and the saline/waste port 18 are placed on an upper portion of the outer housing element 12a. With this layout of the housing 12, the rotating actuator 24 is provided with additional capability for creating specific fluid paths. For example, the second bore 44 (FIG. 2) ends in a vertical groove 45 that reaches from a main lumen level 53 down to an offset port level 54, while the first bore 42 (FIG. 2) terminates in a simple bore hole 58. The offset port level 54 is provided at a lower level to accommodate the contrast bore which extends through the housing 12 from the contrast port 16 to the rotating actuator 24. One example use of this type of configuration is also noted below by reference to FIG. 4B.

Also shown in FIG. 3 are several letters 56. The illustrative letters 56 indicate contrast ("C"), aspiration ("A"), and saline ("S"). The rotating actuator 24 may include a pointer or other indicating device for indicating which of the three letters 56 is being indicated at a particular time. The inclusion of letters 56 allows a user to quickly and easily determine which of the configurations noted below with respect to FIGS. 4A–4C the rotating actuator 24 is positioned for. Thus, when the letter "C" is indicated, the rotating actuator 24 is positioned for the infusion of a contrast medium. The letters may be formed in a manner allowing easy visibility in a low light environment.

FIGS. 4A–4D are schematic cross section representations of a flat rotor design illustrative embodiment showing four operational configurations. FIG. 4A illustrates a first configuration or position for injecting a contrast medium to a catheter or other medical device. As illustrated, the handle 51 is turned with respect to the housing 12 such that the rotating actuator 24 is in a first position. In the first position, fluid pathways are defined between the syringe branch 30a and the first bore 42, between the contrast bore 32 and the second bore 44, and between the main outlet branch 36a and the third bore 46. Two check valves 50, 52 are included in the fluid paths along the contrast bore 32 and main outlet branch 36a for preventing incorrect fluid flow (i.e., aspiration from the catheter port 22 or fluid backflow into the contrast port 16). A pressure/suction device is then attached at syringe port 14, and suction and pressure are alternatingly applied to pull contrast fluid into the manifold 10 from the contrast port 16 and infuse contrast fluid to a medical device attached at the catheter port 22.

FIG. 4B illustrates a second configuration of the manifold 10, this configuration adapted for aspiration of fluid. In particular, the handle 51 has been manipulated so that rotating actuator 24 adopts a second position wherein the third bore 46 is in fluid communication with one of the main outlet branches 36b, while the fourth bore 48 is in fluid communication with one of the syringe branches 30b. While in this position, a pressure/suction device coupled to the syringe port 14 would be used to withdraw fluid from a medical device coupled to the catheter port 22. Such aspiration may be used, for example, after an occlusion, clot, stone or other object is dissolved or broken up during a procedure.

In another embodiment (which is not shown) an additional waste bore may be included in the housing 12 between the second bore 44 as shown in FIG. 4B and the saline/waste port 18, the waste bore including a check valve preventing infusion of saline through the saline/waste port 18. Such a waste bore may be used during an aspiration procedure to allow an operator to remove and dispose of fluids drawn through a medical device coupled to the catheter port 22 quickly and easily. In a further embodiment, a waste bore may also be provided with a stopcock or other controllable valve such that the waste bore may be selectively blocked or opened without changing the second position.

Another aspect of the manifold 10 is illustrated by FIG. 4B in conjunction with FIG. 3. As illustrated in FIG. 3, the saline/waste port 18 and the saline/waste bore 34 are not level with the contrast port 16 and contrast bore 32. The second bore 44 is coupled to a vertical groove 45 (FIG. 3) which allows it access at both an upper level for the main lumen level 53 (FIG. 3) and a lower level where the contrast bore 32 passes through the inner housing 12b (FIG. 3). The first bore 42 is approximately aligned with the contrast bore 32 when the rotating actuator 24 is in the second position. However, because the first bore 42 has a first bore hole 58 (FIG. 3) rather than a vertical groove 45 (FIG. 3), the rotating actuator 24 does not allow fluid communication between the first bore 42 and the contrast bore 32 in the second position of FIG. 4B.

FIG. 4C illustrates the manifold 10 in a third configuration having the rotating actuator 24 in a third position, as controlled by the handle 51. In the third configuration, the syringe branch 30a is in fluid communication with the fourth bore 48, and the saline/waste branch 34 is in fluid communication with the second bore 44. This positioning places a pressure/suction device coupled to the syringe port 14 in fluid communication with the saline/waste device attached to the saline/waste port 18. This position allows the pressure/suction device to be used to flush out the manifold 10 as well as the pressure/suction device itself. Saline is drawn through the saline/waste port 18 into the manifold 10 and the pressure/suction device itself, and then returned through the saline/waste port 18 as waste.

FIG. 4D illustrates another position for infusing saline from a pressurized saline source. The stopcock 26 has been turned to a different position from that shown in any of FIGS. 4A–4C. As illustrated, the stopcock 26 as turned allows pressurized saline to enter via the saline/waste port 18, pass through pressurized saline bore 40, through the stopcock 26 and into the auxiliary bore 38, from which it reaches the main outlet bore 36 and is infused through a medical device coupled to catheter port 22. During this process, the auxiliary port 20 may be used as a pressure monitoring port or a medicine or other substance infusing port.

Figure 5:
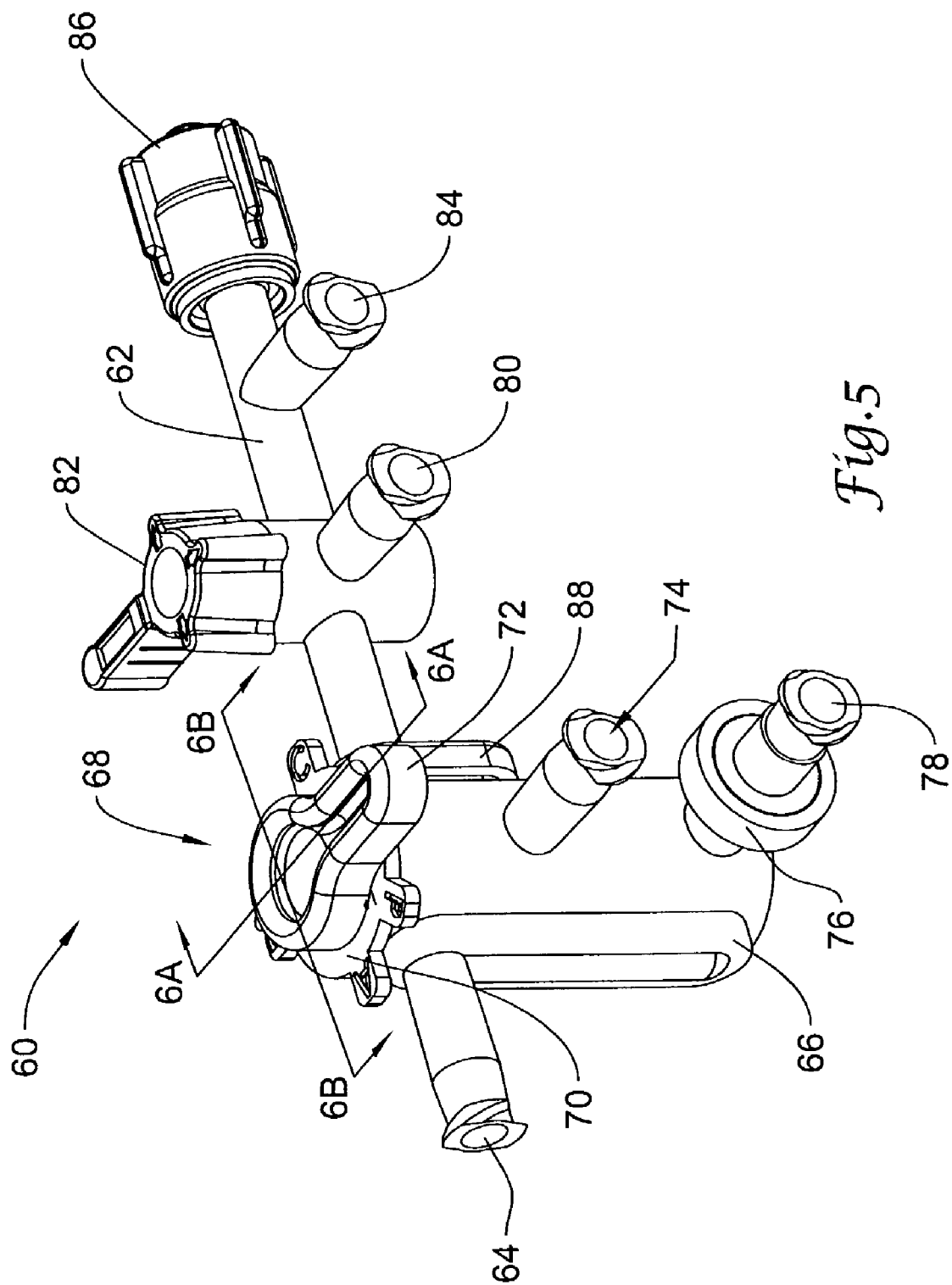
FIG. 5 is a perspective view of a second illustrative embodiment also having a rotating actuator in a more vertical design than that of FIG. 1.

FIG. 5 is a perspective view of a second illustrative embodiment having a rotating actuator in a more vertical design than that of FIG. 1. The manifold 60 of FIG. 5 includes a main bore 62 extending along the majority of its length, beginning at syringe port 64 which couples to the syringe bus line 66. The syringe bus line 66 provides a location where a number of bores are fluidly connected together in a common location. The syringe bus line 66 is attached to the actuator housing 68, which includes an indicator plate 70 and a bore for receiving the rotary actuator 72. The rotary actuator 72 provides selective coupling between the several bores and ports which interact with the actuator housing 68. The indicator plate 70 includes letters indicating which of several positions the rotary actuator 72 is in, for example, "C" indicates a contrast infusion position, "F" indicates a flush position, "A" indicates an aspiration position, and "P" indicates a position for infusion of pressurized saline. By turning the rotating actuator 72 in the actuator housing 68, each of these positions may be reached.

The actuator housing 68 is illustrated as including a saline/waste port 74 and a check valve 76 which couples to a contrast port 78. The check valve 76 prevents back-flow of fluid to a contrast medium source coupled to the contrast port 78. A main bus 88 is included on the actuator housing 68, the main bus 88 being adapted to allow fluid transfer between multiple bores/openings in the actuator housing 68, as will be explained further below. The main bore 62 is coupled through the main bus 88 to the actuator housing 68.

The main bore 62 proceeds to a medication port 80 which is coupled to the main bore 62 via a three way stopcock 82 which can be turned to select various different combinations of fluid passageways. In the illustrated position, the stopcock 82 couples the medication port 80 to the main bore 62 without blocking the main bore. As can be appreciated by one of skill in the art, the stopcock 82 may be rotated by partial turns of about ninety degrees, a first turn couples the medication port 80 to the catheter port 86 while blocking off the main bore 62 going toward the actuator housing 68; another turn of ninety degrees would block out the medication port 80 while leaving the main bore 62 open along its length; and a third turn of ninety degrees would couple the medication port 80 to the actuator housing 68 while blocking the main bore 62 going toward the pressure transducer port 84 and catheter port 86. The main bore 62 further extends to a transducer port 84 and catheter port 86.

While the above description of the various ports in the design names certain ports, for example the medication port 80, these designations should be understood as merely examples of how the ports may be coupled. Other devices may be coupled at various locations; for example, the medication port 80 could instead be used to couple to a pressurized saline source such that, with the stopcock 82 turned ninety degrees from the illustrated position, a pressure transducer could be placed at transducer port 84, and pressurized saline injected to a medical device coupled to catheter port 86 with the pressure level monitored by the transducer. It should also be noted that either the medication port 80 or the transducer port 84 may be used as an auxiliary port similar to auxiliary port 20 explained above with reference to FIG. 1.

Figure 6A:
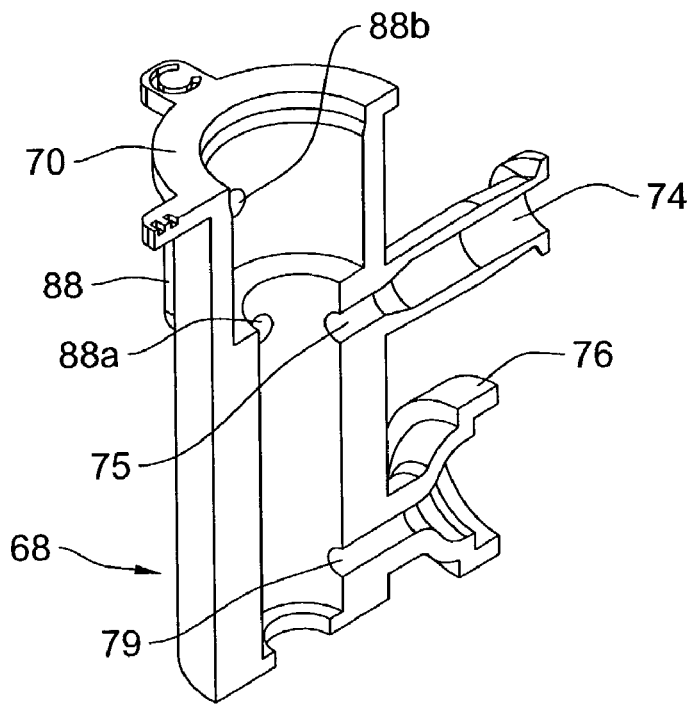
FIGS. 6A–6B are cut-away cross sectional views at different angles of the actuator housing illustrated in FIG. 5.
Figure 6B:
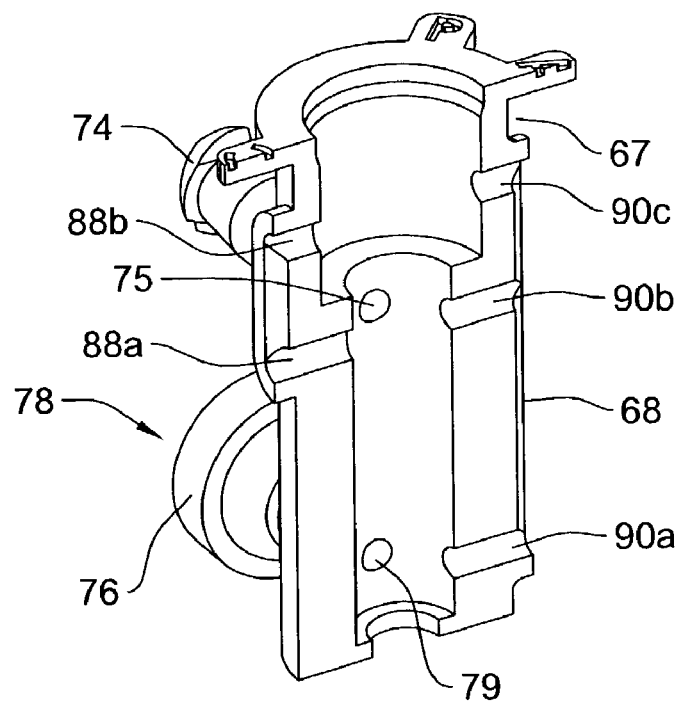

FIGS. 6A and 6B are cut-away cross-sectional views at different angles of the actuator housing 68 illustrated in FIG. 5. FIG. 6A illustrates a cross section taken along line 6A–6A in FIG. 5. The actuator housing 68 includes an indicator plate 70 as explained above. Also illustrated is a saline/waste opening 75 which leads out to the saline/waste port 74, and a contrast opening 79 which leads out to a check valve 76 that, in turn, would lead to a contrast port 78 (not shown). A portion of the main bus 88 is illustrated as well, with first main opening 88a and second main opening 88b providing fluid communication to the main bus 88 from inside the actuator housing 68.

FIG. 6B illustrates a cross section of the actuator housing 68 taken along line 6B–6B in FIG. 5. The actuator housing 68 is shown to illustrate, again, the saline/waste opening 75 and contrast opening 79 as noted above. Also shown are the first main opening 88a and second main opening 88b as noted above. Three syringe bus openings 90a, 90b, 90c are also illustrated, each opening into syringe bus seat 67. The syringe bus openings are adapted to provide fluid communication to the syringe bus 66 illustrated in FIG. 5.

Figure 7A:
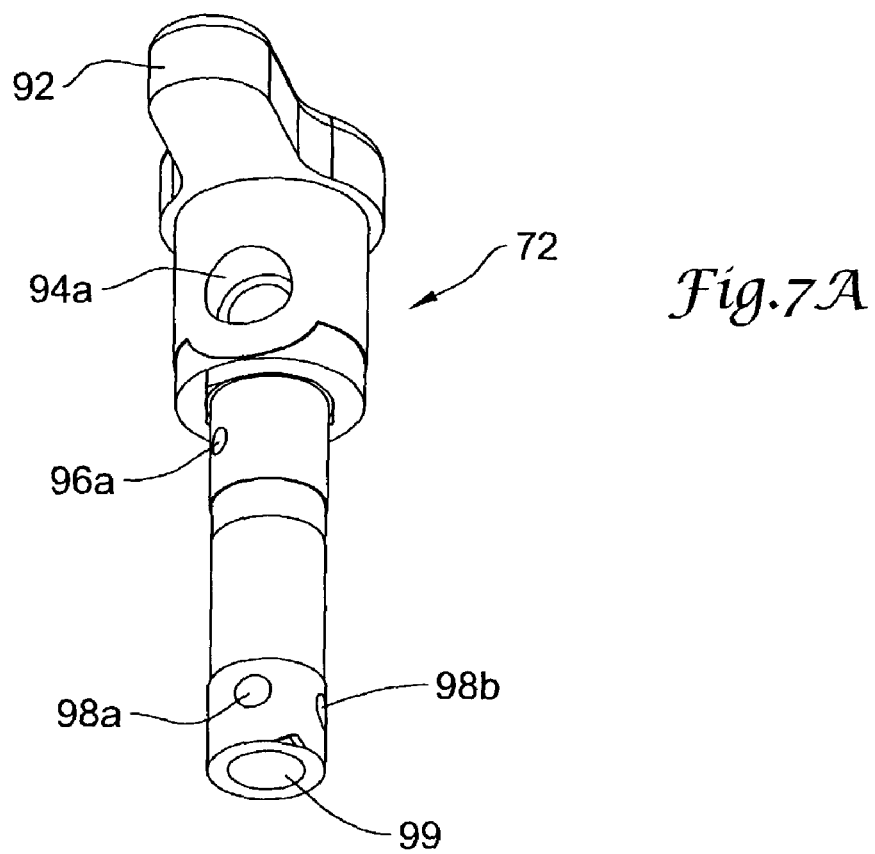
FIGS. 7A–7B are isolated perspective views of the rotary actuator corresponding to the illustrative embodiment of FIG. 5.
Figure 7B:
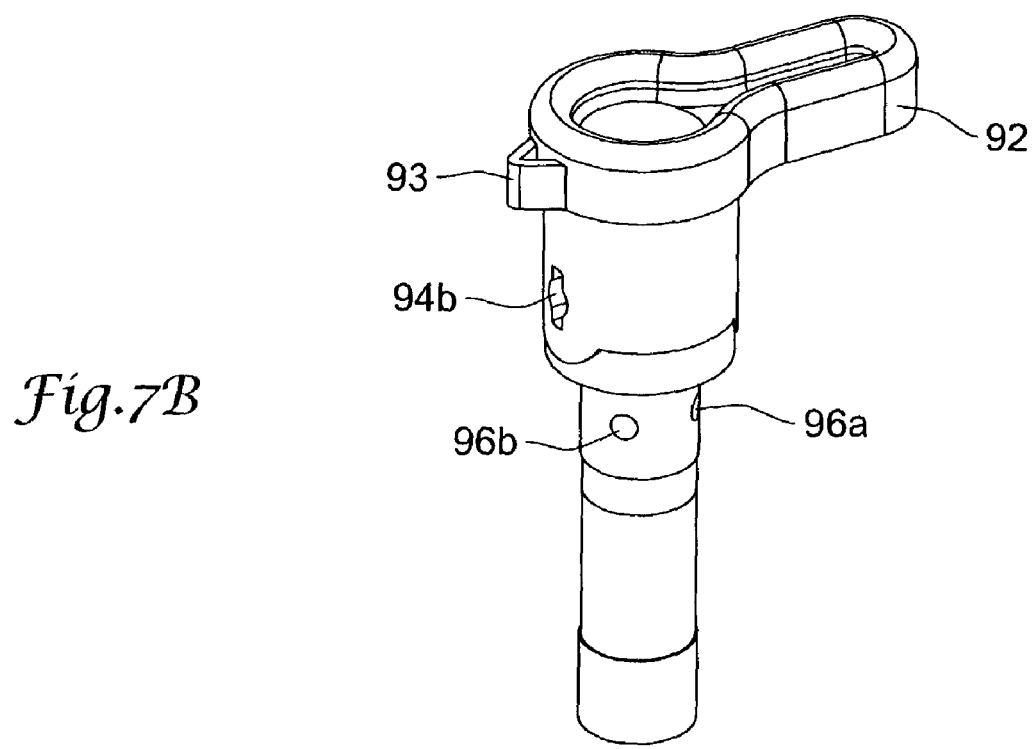

FIGS. 7A–7B are isolated perspective views of the rotary actuator 72 corresponding to the illustrative embodiment of FIG. 5. FIG. 7A illustrates the rotary actuator 72 as including first bore opening 94a, third bore opening 96a, fifth bore opening 98a and sixth bore opening 98b. The fifth and sixth bore openings 98a, 98b are fluidly connected through the shaft of the rotary actuator 72. A handle 92 is included for manipulating the position of the rotary actuator 72. FIG. 7B illustrates another perspective view from a different angle, this time also showing an indicator 93 opposite the handle 92, the indicator 93 being aligned with respect to the various openings such that the indicator 93 and indicator plate 70 (FIG. 5) provide an indication of which configuration the manifold is in. The second bore opening 94b is also shown, such that the first and second bore openings 94a, 94b are on opposing sides of the shaft and fluidly connected therebetween by a check valve allowing fluid flow in only one direction.

It can be seen from viewing FIGS. 5, 6b, and 7a–7b together that when the indicator 93 is over the "C" or the "A" of the indicator plate 70, the first and second bore openings 94a, 94b (with a bore and check valve therebetween) provide fluid communication between the second main bus opening 88b and the third syringe bus opening 90c. The check valve is aligned between the first and second bore openings 94a, 94b such that when the indicator 93 is over the "A", fluid flow is allowed from the main bus 88 to the syringe bus 90, and when the indicator 93 is over the "C", fluid flow is allowed from the syringe bus 90 to the main bus 88. Thus, when so aligned, the rotary actuator 72 allows selective, one-way fluid communication between the syringe port 64 and the main bore 62. Meanwhile, if the indicator 93 is over either the "P" or the "F", the first and second bore openings 94a, 94b do not provide a fluid path from the syringe port 64 to the main bore 62.

It can also be seen from viewing FIGS. 5, 6b and 7a that with the indicator 93 over the "C" on the indicator plate 70, the fifth bore opening 98a aligns with the first syringe bus opening 98a, and the sixth bore opening 98B aligns with the contrast opening 79, providing a fluid path from the contrast port 78 to the syringe port 64, with the check valve 76 included in the fluid path. Thus, the check valve 76 allows contrast to be drawn to the syringe port 64, but does not allow fluid to be forced out to the contrast port 78. Meanwhile, the check valve between the first and second bore openings 94a, 94b in the rotary actuator 72 allows contrast fluid to be infused to the main bore 62 and the catheter port 86, but does not allow withdrawal of fluid from the main bore 62 toward the syringe port 64. As such, a user may simply turn the handle 92 to manipulate the rotary actuator 72 and put the manifold 60 into a configuration for injecting contrast media to a patient or into a medical device.

When the indicator 93 is turned to cover the "A" on the indicator plate 70, the check valve between the first bore opening 94a and the second bore opening 94b is reversed, while the fifth and sixth bore openings 98a, 98b will not be in alignment with either of the first bus opening 90a or the contrast opening 79, preventing flow of contrast media. Also, while the indicator 93 is over the "A", the second and third bore openings 96a, 96b are misaligned with respect to each of bore openings 88a, 75, and 90b, preventing saline flow as well. The only flow allowed is, therefore, aspiration from the catheter port 86 to the syringe port 64.

When the indicator 93 is turned to cover the "F", the third bore opening 96a is aligned with the saline opening 75, while the fourth bore opening 96b is aligned with the second syringe bus opening 90b. This configuration allows saline to be withdrawn from the saline/waste port 74 to the syringe port 64, and allows fluid from the syringe port 64 to be directed out of the saline/waste port 74. With the indicator 93 over the "F", therefore, the manifold 60 and the pressure/suction device attached to the syringe port 64 may be flushed with clean saline.

When the indicator 93 is over the "P", the third bore opening 96a is aligned with the first main bus opening 88a, and the fourth bore opening 96b is aligned with the saline/waste opening 75. This positioning allows pressurized saline to be injected via the saline/waste port 74 to a medical device coupled to the catheter port 86.

Figure 8:
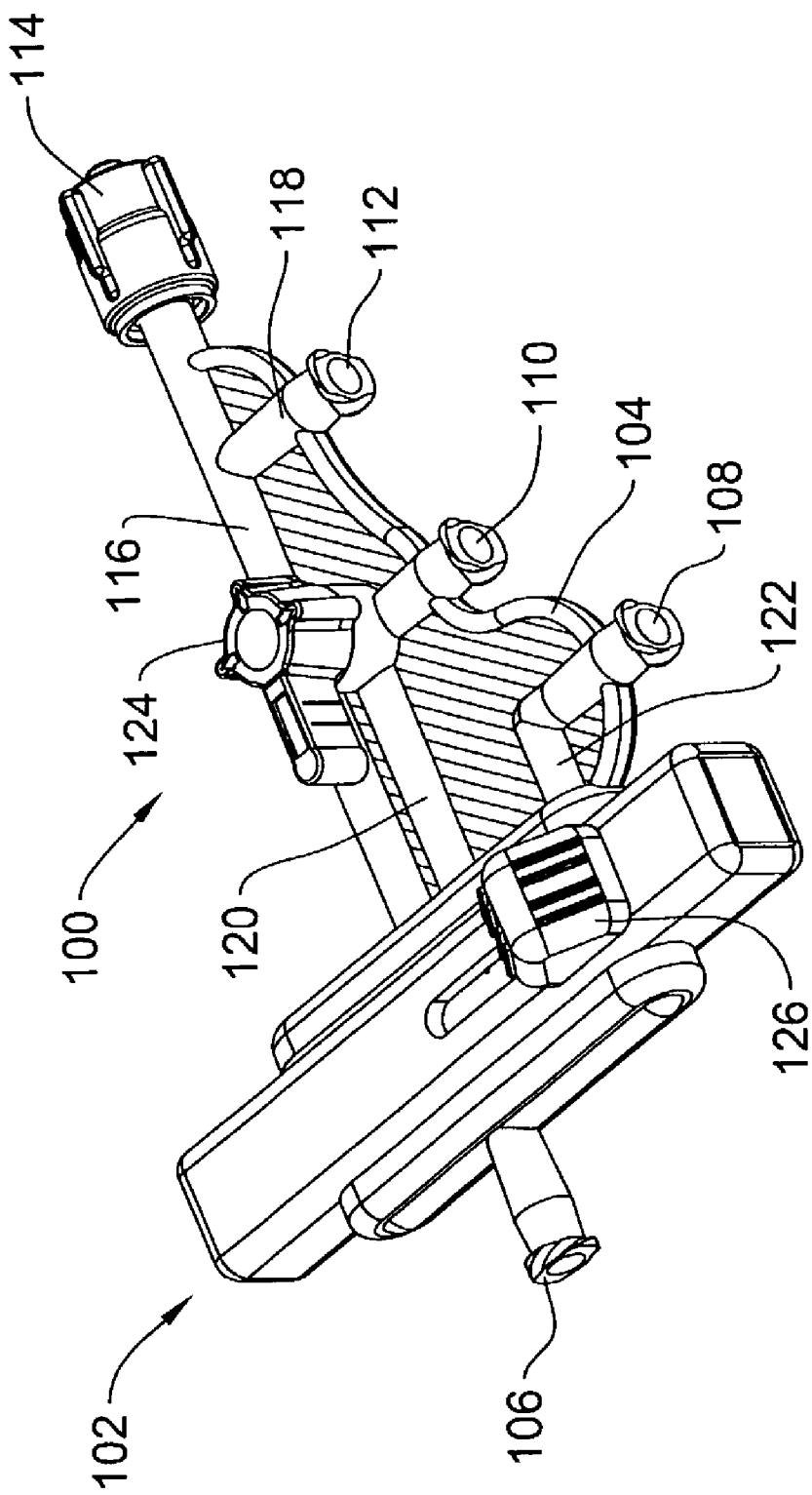
FIG. 8 is a perspective view of a third illustrative embodiment, this time having a sliding actuator.

FIG. 8 is a perspective view of a third illustrative embodiment, this time having a sliding actuator. The manifold 100 includes a slider housing 102 and a port housing 104. A syringe port 106 is provided opposite the slider housing 102 from the port housing 104. The port housing includes contrast port 108, saline/waste port 110, auxiliary port 112, and catheter port 114. The catheter port 114 is in fluid communication with a main bore 116, which is directly accessed from the auxiliary port 112 via an auxiliary bore 118. The saline/waste port 110 is coupled to the slider housing 102 by a saline/waste bore 120, and the contrast port 108 is coupled to the slider housing 102 by a contrast bore 122. The operation of the manifold 100 is generally controlled by two main valve pieces: a three-way stopcock 124 is an optional piece that may be used in conjunction with a pressurized saline source in certain applications, and a slider apparatus is included and coupled to a slider button 126 for controlling which of several configurations is in use. The ports may connect to various devices in similar fashion to that explained above with reference to the auxiliary port 20 of FIG. 1.

Figure 9:
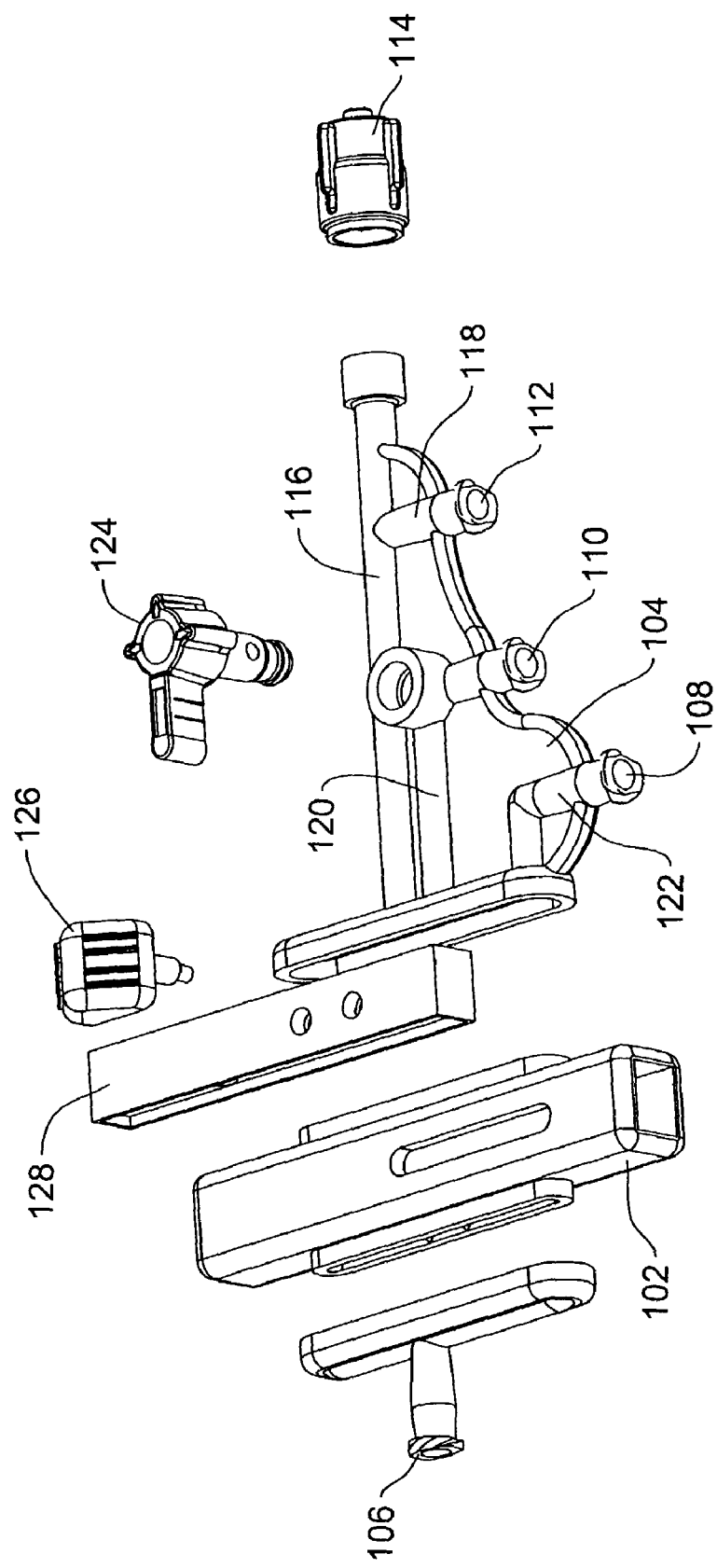
FIG. 9 is an exploded view of the various parts of the illustrative embodiment of FIG. 8.

FIG. 9 is an exploded view of the various parts of the illustrative embodiment of FIG. 8. As illustrated, the port housing 104 includes the ports 108, 110, 112 which may be formed thereon in an injection molding process, or the port housing 104 may be an integrally formed piece from several individual pieces, though the port housing 104 may be formed by any suitable means. The catheter port 114 is illustrated in the form of a rotating adaptor that is used to allow rotation of the manifold relative to the catheter. This is a feature that may be included in some embodiments, while other adaptors and ports may also be used. The stopcock 124 is inserted and held in place in port housing 104, and may be a three-way valve in some embodiments.

In some embodiments, the port housing 104 is formed by making the bores 116, 118, 120, 122 first (for example by an extrusion and later bending or attachment process), and placing the bores in a mold and inserting a plastic substance around the bores to couple the port housing 104 together. The slider housing 102 is then snap fit to the port housing 104 after a slider actuator 128, which includes a number of valves built therein, is placed into a groove in the port housing 104. The slider button 126 is attached to the slider actuator 128 for controlling the positioning of the slider actuator 102. The syringe port 106 may also be snap fit into place. Adhesives, screws, rivets, heat curing/bonding processes or any other suitable process may also be used to bond the various pieces together. The slider housing 102 may include end members for snap fitting thereon after the slider actuator 128 is placed within the channel or groove of the slider housing 102.

Figure 10:
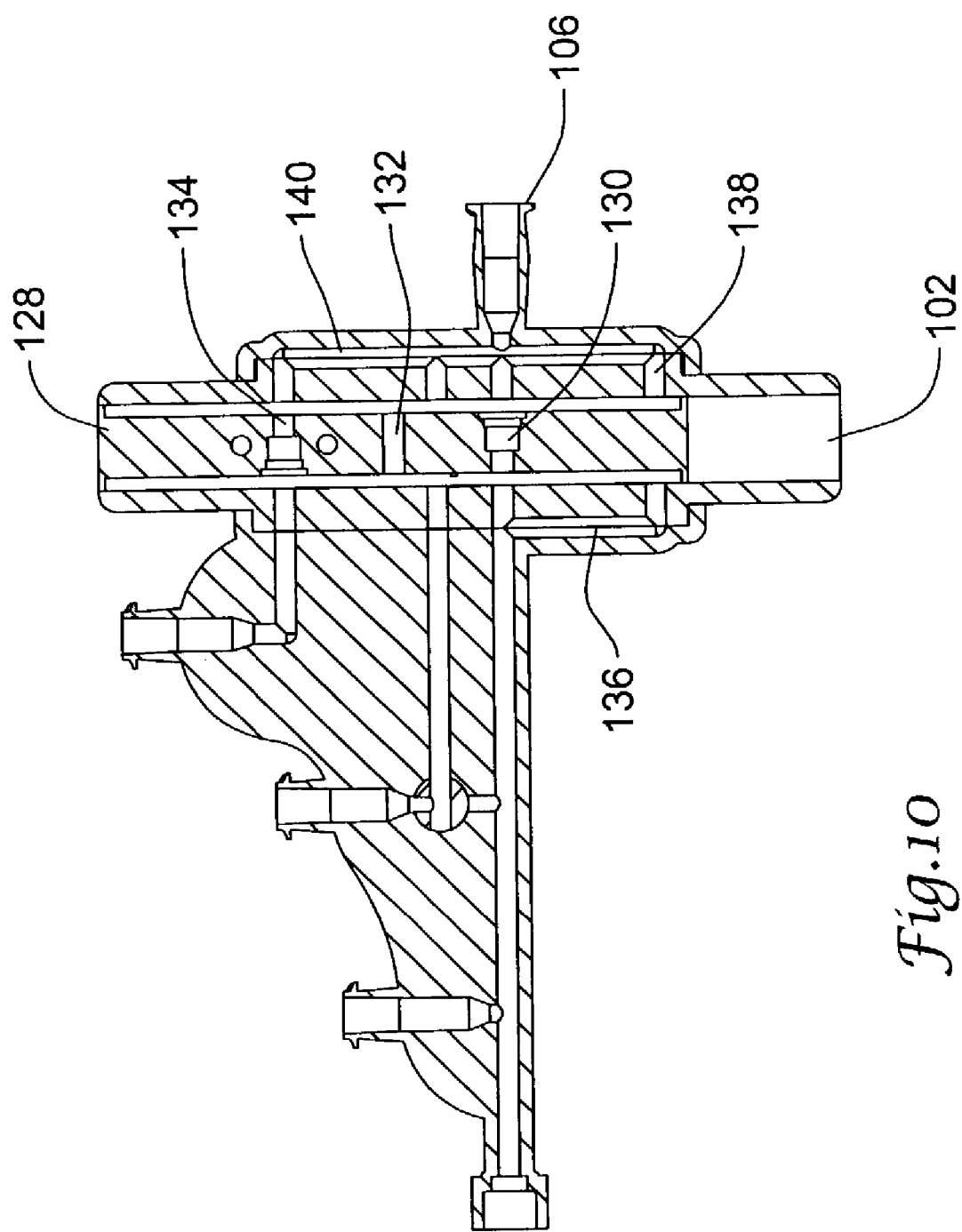
FIG. 10 is a cross-sectional view of the illustrative embodiment of FIG. 8.

FIG. 10 is a cross-sectional view of the illustrative embodiment of FIG. 8. The cross-sectional view highlights the characteristics of the slider actuator 128 and the slider housing 102. In particular, the slider actuator 128 includes a first check valve 130, an open valve 132, and a second check valve 134. The first check valve 130 and second check valve 134 are both one-way valves, but are disposed on the slider actuator 128 in opposing directions. The slider housing 102 includes a first bore 136, a second bore 138 and a third bore 140. These bores provide additional fluid paths within the slider housing which, in conjunction with the slider actuator 128, provide some of the operational advantages of the manifold 100. The interplay between the bores 116, 120, 122, 136, 138, 140, the valves 130, 132, 134, and the syringe port 106, is further explained below by reference to FIGS. 11A–11D.

Figure 11A:
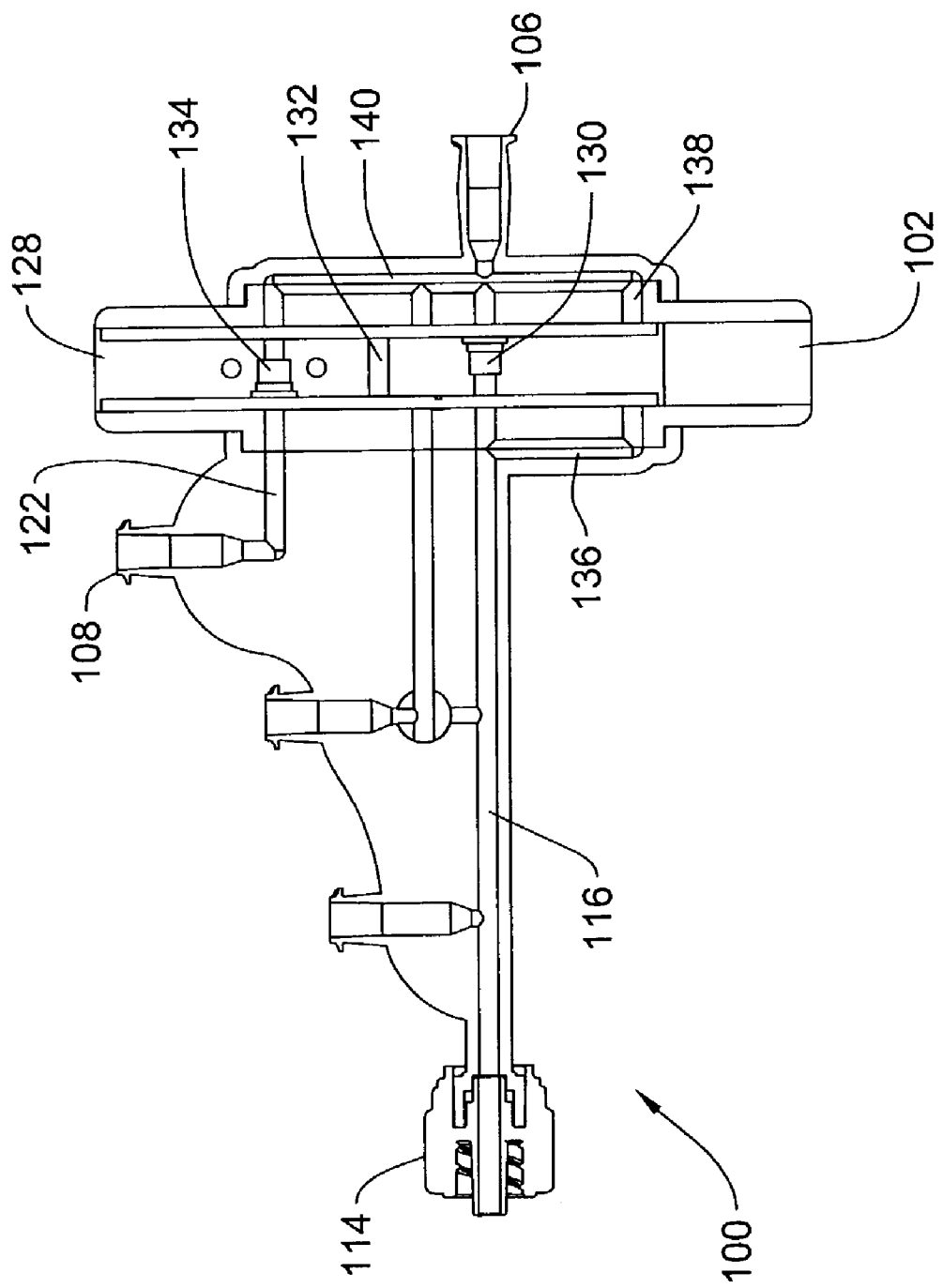

FIGS. 11A–11D are schematic cross section representations of the slider design of FIG. 8 showing four operational configurations. FIG. 11A illustrates the manifold 100 in a first configuration, having the slider actuator 128 in a first position. With the slider actuator 128 in the first position, the contrast port 108 is coupled via the contrast bore 122, and the second check valve 134 is coupled to the third bore 140 in the slider housing 102. The third bore 140 couples to the syringe port 106. Also, with the slider actuator 128 in the second position, the third bore 140 is coupled to the first check valve 130 which, in turn, is coupled to the main lumen 116 of the manifold 100. The main bore 116 is connected to the catheter port 114.

The first position is a contrast infusion position which functions as follows. When a pressure/suction device such as a syringe is coupled to the syringe port 106 and suction is applied, the first check valve 130 prevents flow from the main bore 116 to the third bore 140, but the second check valve 134 allows flow from the contrast bore 122 (and hence contrast port 108) to the third bore 140, so that contrast may flow out through the syringe port 106. After suction is applied to bring contrast out through the syringe port 106, positive pressure is then applied through the syringe port 106. With pressure applied at syringe port 106, the second check valve 134 prevents back flow into the contrast bore 122, but the first check valve 130 allows the contrast to be infused to main bore 116 and out through the catheter port 114. Note that the open valve 132 is not aligned with any bore or opening through the slider housing 102, so that other fluid flow paths are blocked.

FIG. 11B illustrates a second configuration of the manifold 100, this time with the sliding actuator 128 in a second position relative to the slider housing 102. In the second position, the open valve 132 provides a fluid connection between the saline/waste bore 120 and the third bore 140. The first valve 130 and third valve 134 are not aligned with any other bore and, therefore, additional possible fluid paths are blocked. The saline/waste port 110 may be coupled to a combination saline source and waste reservoir device which may include an internal double check valve system allowing saline to be withdrawn and directing infused fluids to a waste receptacle. When suction is applied via the syringe port 106, saline is allowed to flow from the saline/waste port 110 through the saline/waste bore 120, open valve 132, and third bore 140 so the saline exits via the syringe port 106. When pressure is applied via the syringe port 106, fluid flows through the third lumen 140, across the open valve 132, into saline/waste bore 120, and out of the manifold 100 through the saline/waste port 110. The sequential application of suction and pressure flushes the manifold 100 of any waste between separate steps of a procedure. For example, after injecting contrast, an operator may want to flush the manifold 100 of contrast before aspirating blood or other fluids.

Figure 11C:
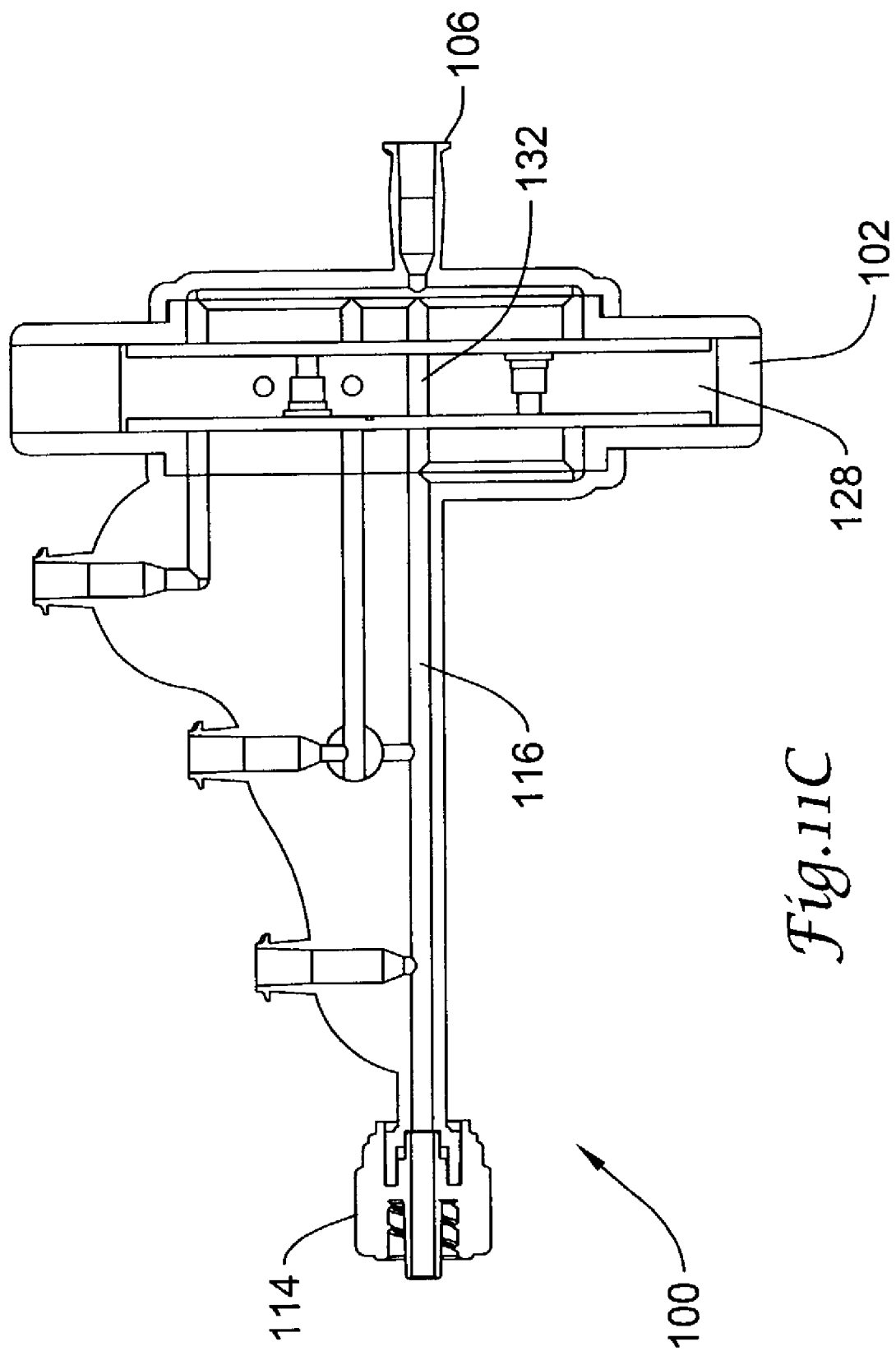

FIG. 11C illustrates a third configuration of manifold 100, this configuration being adapted for aspiration of fluid from a medical device coupled to the catheter port 114. In the third configuration, the sliding actuator 128 is in a third position with respect to the slider housing 102 such that the open valve 132 couples the main bore 116 to the syringe port 106. The third position allows for aspiration of a fluid from a medical device coupled to the catheter port 114. Such aspiration may be used, for example, to clear the catheter and manifold of any air either after a catheter exchange takes place, prior to catheter insertion, or after a period of non-use in a medical procedure. For example, it is often considered appropriate to aspirate the catheter/manifold after two minutes where no fluid is infused or aspirated during a procedure in order to clear any air bubbles or blood clots that may form during such time.

Figure 11D:
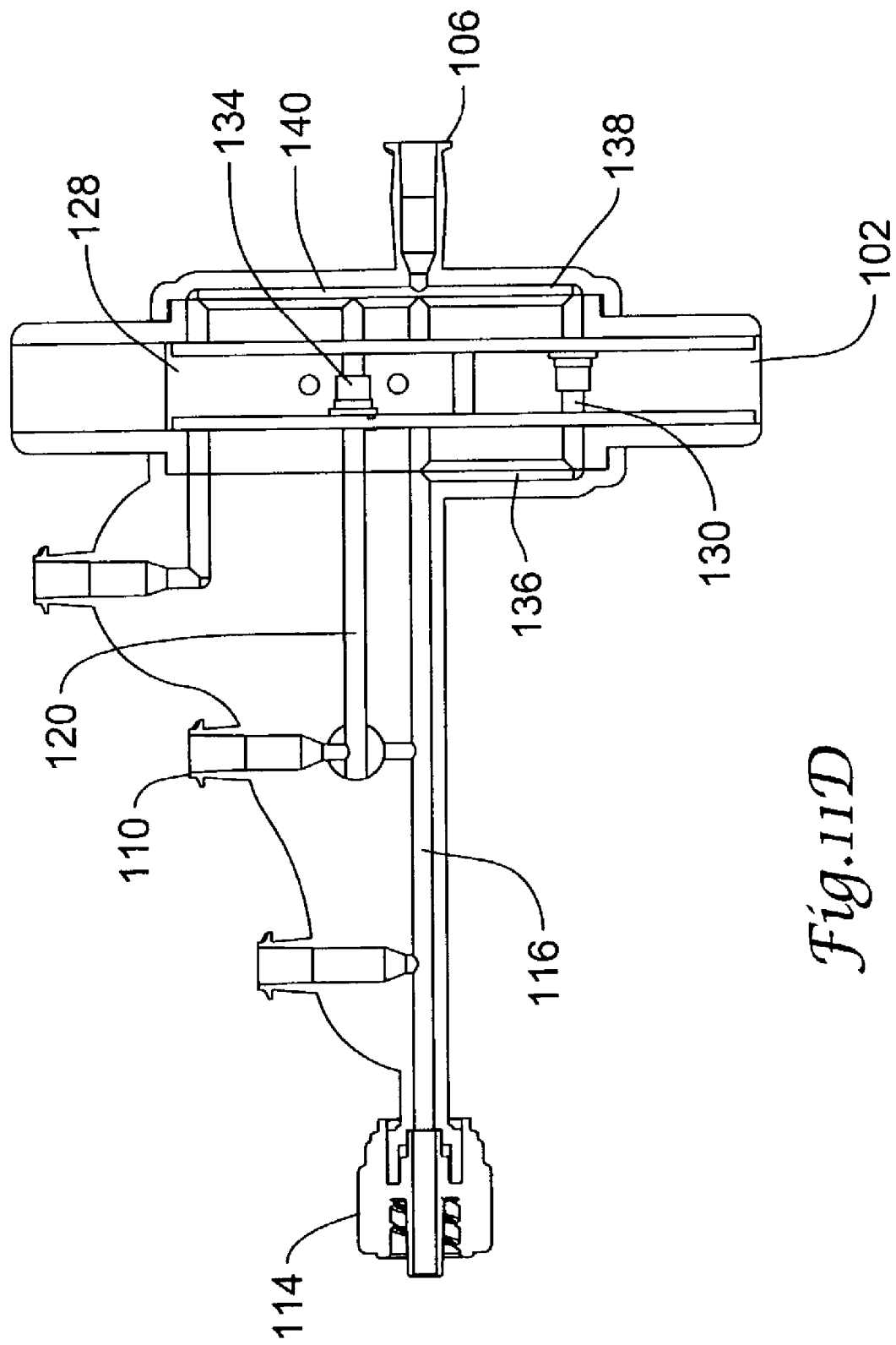

FIG. 11D illustrates a fourth configuration of manifold 100, this configuration adapted for infusing a saline solution while blocking back-flow from a medical device coupled to catheter port 114. In the fourth configuration, the sliding actuator 128 has been moved such that the first check valve 130 couples the first bore 136 to the second bore 138, while the second check valve 132 couples the third bore 140 to the saline/waste bore 120. When suction is applied via the syringe port 106, saline flows from the saline/waste port 110 through the saline/waste bore 120, second check valve 134, and third bore 140 out to the suction/pressure device via the syringe port 106. Note that as suction is applied, the first check valve 130 prevents fluid from flowing from the catheter port 114 through main bore 116. When pressure is applied via the syringe port 106, the second check valve 134 prevents saline from flowing back up to the saline/waste port 110 and bore 120, while the first check valve 130 allows saline to be infused to a medical device coupled at the catheter port 114 via the main bore 116 and the first bore 136. This step may also be used to clear out the main bore 116 between procedures, for example, if nothing is coupled to the catheter port 114, saline may be passed through the main bore 116 until it runs clear.

Figure 12:
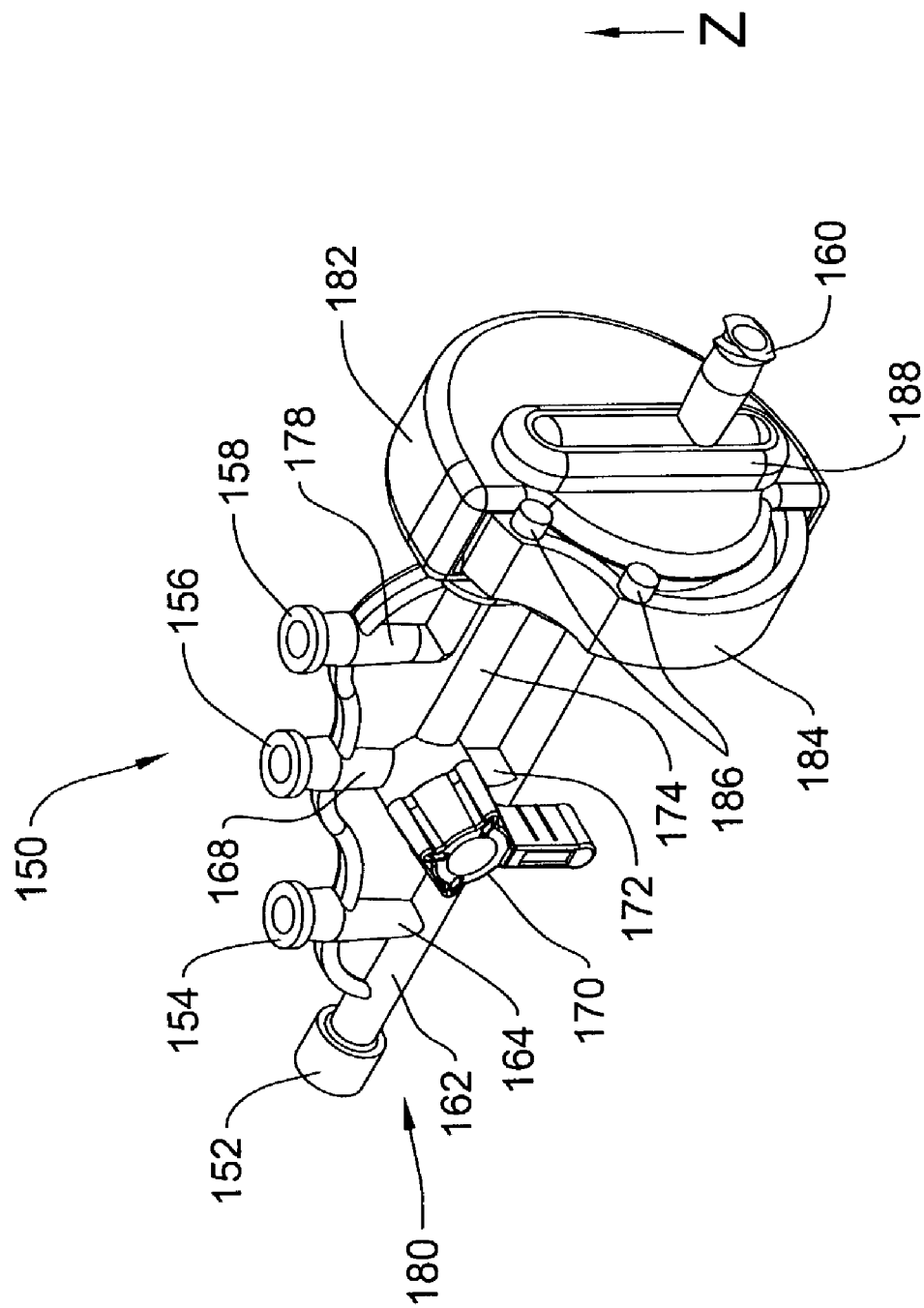
FIG. 12 is a perspective view of a fourth illustrative embodiment making use of a rotary valve concept.

FIG. 12 is a perspective view of a fourth illustrative embodiment making use of a rotary valve concept. For the purposes of illustration and clarity, reference direction Z is defined in each of FIGS. 12, 13, 15A–15B and 16, such that the relative alignment of various parts in the illustrative embodiment may be clear.

The manifold 150 provides several illustrative ports, including a catheter port 152, an auxiliary port 154, a saline/waste port 156, a contrast port 158, and a syringe port 160. These ports may be adapted for and used in a variety of ways including those noted above with respect to the various ports shown in FIG. 1. The ports are coupled to various bores, including a main bore 162 coupled to the catheter bore 152, and an auxiliary bore 164 coupled to the auxiliary port 154. The saline/waste port 156 is coupled to a saline/waste bore 168 that reaches a junction defined at a stopcock 170. Depending on the position of the stopcock 170, the saline/waste bore 168 may couple to a pressurized saline infusion bore 172 that couples into the main bore 172, and/or a saline/waste branch 174 that runs in the other direction. The contrast port 158 is coupled to a contrast bore 178.

Together, the ports and bores (except the syringe port 160) are attached, coupled or molded together by any suitable manner to form a port housing 180. Attached to the port housing 180 is the rotor housing 182 which houses a rotary actuator 184. The rotary actuator 184 includes stops 186 for helping to maintain a chosen position in the rotor housing 182. A syringe bus 188 couples to the syringe port 160 and is attached by any suitable manner to the rotor housing 182.

The stopcock 170 may be used to provide a direct saline infusion fluid path by allowing the saline/waste bore 168 to couple with the pressurized saline infusion bore 172 and access the main bore 162. This positioning may be achieved with or without allowing fluid flow through the saline/waste branch 174. During such pressurized infusion, the auxiliary port 154 may be provided with a pressure transducer or other sensor to allow the pressure or other condition of infused fluid to be monitored easily. Other functions may also be performed in conjunction with pressurized saline infusion, including, for example, the provision of medicine or contrast media through the auxiliary port 154.

Figure 13:
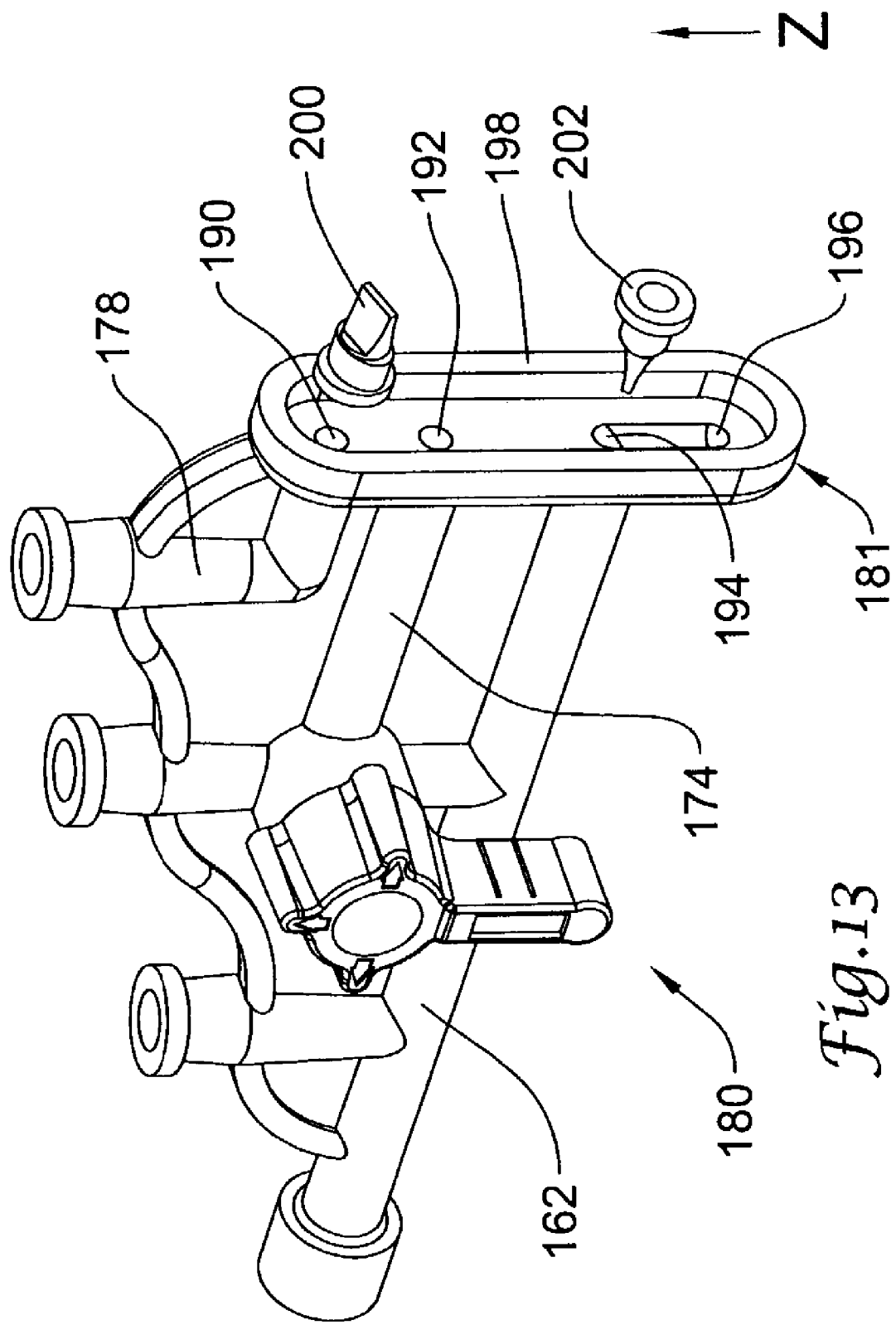
FIG. 13 is a perspective view of the illustrative embodiment of FIG. 12 with several pieces removed.

FIG. 13 is a perspective view of the illustrative embodiment of FIG. 12 with several pieces removed. The view focuses mainly on the port housing 180 and the rotor housing receiver 181. The rotor housing receiver 181 includes several access holes. For example, the contrast bore 178 is provided with a first access hole 190, and the saline/waste branch 174 is provided with a second access hole 192. A third access hole 194 is provided for the main bore 162, with an access bus 196 also provided. The rotor housing receiver 181 includes a collar 198 for providing a securing location, for example, for use of an adhesive, welding technique, or snap fit, to attach a rotor housing 182 such as that shown in FIG. 12.

Also illustrated in FIG. 13 are a first check valve 200 and a second check valve 202. As explained below, the first check valve 200 is provided on the rotary actuator (not shown) in order to prevent contrast media from backflowing into the contrast lumen 178 through the first access hole 190. The second check valve 202 is provided on the rotary actuator (not shown) to prevent aspiration of fluid from the main lumen 162 during a contrast media infusion step. The check valves 200, 202 are illustrated in the position each adopts when the rotary actuator (not shown) is positioned for contrast infusion.

Figure 14:
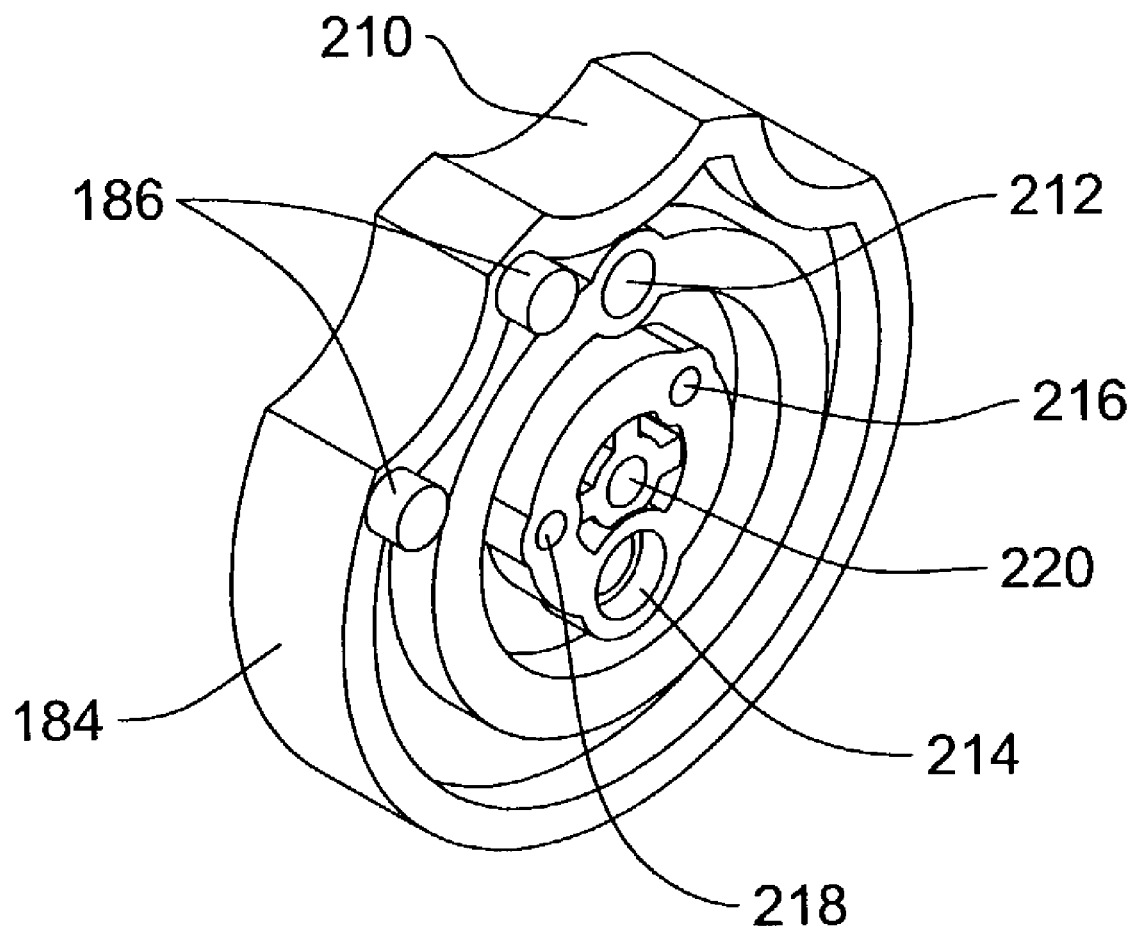
FIG. 14 is a schematic view of the rotary valve of FIG. 12.

FIG. 14 is a schematic view of the rotary actuator of FIG. 12. The rotary actuator 184 includes stops 186 for accurate positioning. Thumb grooves 210 are also provided to enable accurate positioning during a procedure. Any appropriate structure may be used in place of the grooves 210, such as a thumb tab, lever, raised bump, etc. A first check valve seat 212 and second check valve seat 214 are shown as corresponding to opposing sides of the generally circular rotary actuator, such that a diametric line through each of the check valve seats 212, 214 passes through the pin hole 220 of the rotary actuator 184. The check valve seats 212, 214 are adapted to receive the check valves 200, 202 shown in FIG. 13 for use during a contrast media infusion step. A first bore hole 216 and second bore hole 218 are also shown. Each of the check valve seats 212, 214 and bore holes 216, 218 are illustrated on raised portions of the rotary actuator 184. By providing raised and lowered portions on the rotary actuator, fit seals can be created around the check valve seats 212, 214 and bore holes 216, 218, without making it unduly difficult to turn the rotary actuator 184 within a rotor housing.

Figure 15A:
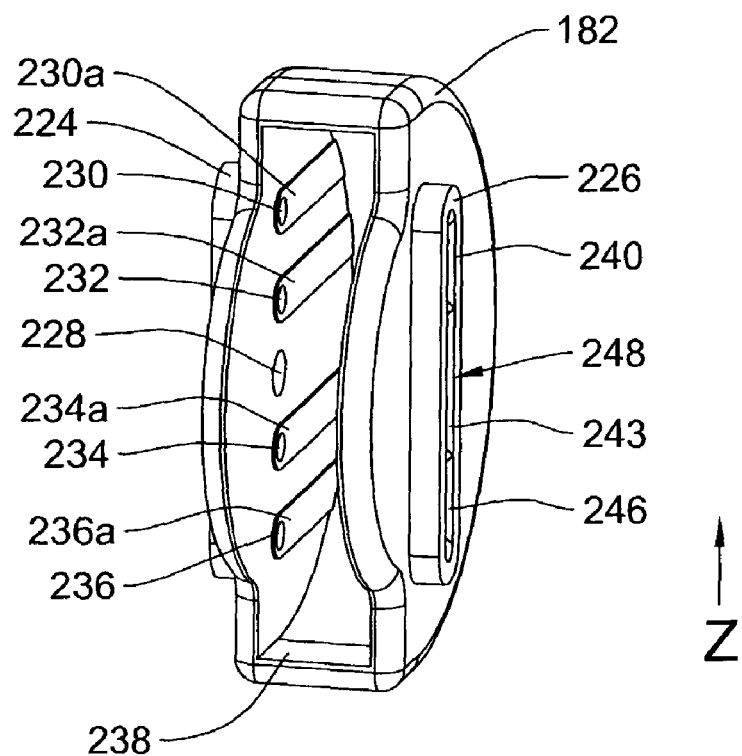
FIGS. 15A–15B are perspective views of the valve housing of FIG. 12.
Figure 15B:
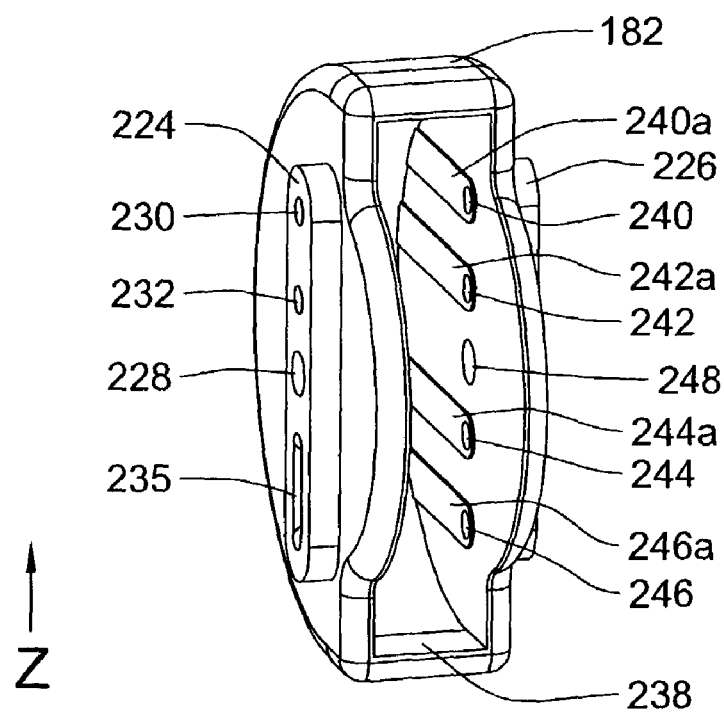

FIGS. 15A–15B are perspective views of the rotor housing of FIG. 12. FIG. 15A illustrates the rotor housing 182 from an angle allowing the interior of the rotor housing 182 corresponding to the port housing (not shown) side of the rotor housing 182. The rotor housing 182 includes a rotor slot 238 sized to receive a rotary actuator such as the rotary actuator 184 illustrated in FIG. 14. A housing coupler 224 is provided for fitting into the rotor housing seat shown in FIG. 13. A pin hole 228 is also provided, with another pin hole 248 not visible. Once a rotor is placed within the rotor housing 182, a pin may be passed through the pin holes 228, 248 to provide an axis location for the rotor within the rotor housing 182. Such a pin may be snap fit within channel 243 or may be threaded into place using a thread receiver in one of the pin holes 228, 248. Any other suitable mechanism may also be used to hold a pin in place in the pin holes 228, 248.

The rotor housing 182 includes a first hole 230 with a first seal ridge 230a, a second hole 232 with a second seal ridge 232a, a third hole 234 with a third seal ridge 234a, and a fourth hole 236 with a fourth seal ridge 236a. Each of the seal ridges is provided such that, along with the raised and lowered portions of the rotary actuator shown in FIG. 14, a limited area seal is provided without unduly restricting the movement of the rotary actuator within the rotor housing 182. On the syringe side of the rotor housing, the rotor housing also includes a fifth hole 240 and an eighth hole 246, with a channel 243 therebetween extending through a syringe port coupler 226.

FIG. 15B is another perspective view of the rotor housing 182, this time turned to highlight the interior corresponding to the syringe side of the rotor housing 182. The housing coupling 224 is shown to include holes 230 and 232 which are numbered to correspond to the same holes as illustrated in FIG. 15A. Likewise, the fifth hole 240 and the eighth hole 246 are shown in similar fashion. A sixth hole 242 and a seventh hole 244 are also illustrated, these holes, along with a pin hole 248, all being joined to the channel 243 (FIG. 15A). Four more seal ridges 240a, 242a, 244a, 246a are again shown, each being provided for similar reasons as those noted above with respect to seal ridges 230a, 232a, 234a and 236a in FIG. 15A.

Looking now at FIG. 15B in conjunction with FIG. 13, the first hole 230 (FIG. 15B) is provided at a location which, when fully assembled, corresponds to the contrast hole 190 (FIG. 13). The second hole 232 (FIG. 15B) is provided at a location to correspond to the saline/waste hole 174 (FIG. 13). Looking at FIG. 15A as well, the third hole 234 and fourth hole 236 are combined together within the rotor housing 182 to provide a housing bus 235, which corresponds to the location of the main bore bus 196.

Figure 16:
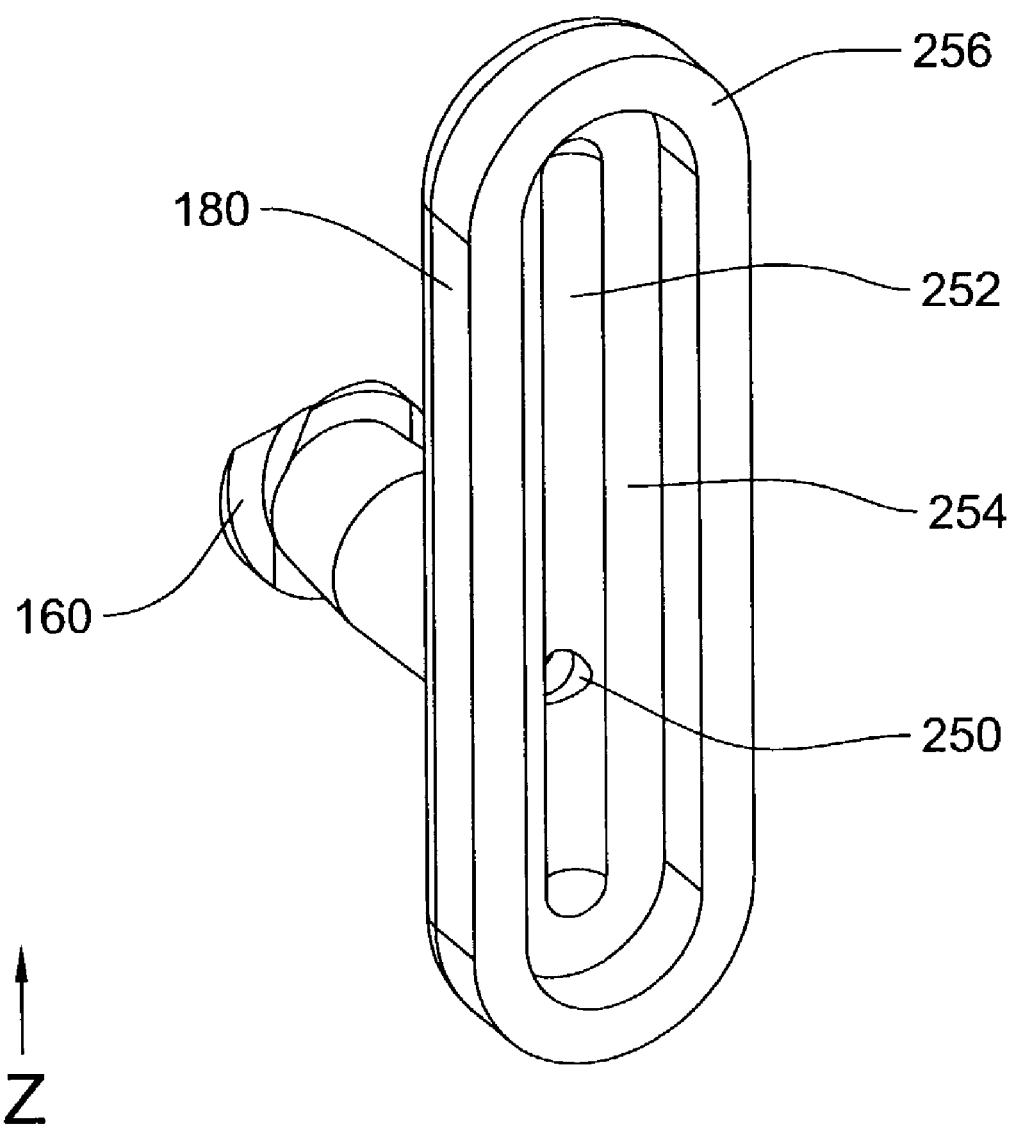
FIG. 16 is a perspective view of a pressure/suction port for the illustrative embodiment of FIG. 12.

FIG. 16 is a perspective view of a syringe receiver 180 for the illustrative embodiment of FIG. 12. The syringe receiver 180 includes a syringe port 160 which is coupled via an opening 250 to a channel 252 defined by channel face 254. The channel face 254 is adapted to provide a seal over the outer face of the syringe coupler 226 (FIG. 15A). Also included is a receiver collar 256, which may be sized and adapted to provide a snap fit over the syringe coupler 226 (FIG. 15A), though adhesive, welding or any other suitable attachment process may also be used. The use of the channel 252 places each of the openings on the syringe side of the rotor housing 182 (holes 240, 246 and channel 243) in fluid communication with the syringe port 160.

The functioning of the rotary embodiment of FIG. 12 will now be explained with reference to several elements of the figures. A first position is when the stops 186 are to their highest position as shown in FIG. 12. When in this position, the check valve seats 212, 214 (FIG. 14) align with the first and third openings 230, 234 in the rotor housing 182 on one side, and the fifth and seventh openings 240, 244 on the other side. This configuration creates the following fluid paths: with suction applied at the syringe port 160, fluid enters from the contrast port 158 to the contrast bore 178, to the contrast opening 190 through the first hole 230, into the first check valve 200 to the fifth hole 240, to the channel 252 through the opening 250, and out the syringe port 160, and, when pressure is applied, in from the syringe port 160, through the opening 250 into the syringe channel 252, out through the housing channel 243 to the seventh hole 244, through the second check valve 202 to main bus 196 and main bore hole 194, to main bore 162 and out through the catheter port 152. Note that, in the given configuration, neither path may be reversed, since the check valves 200, 202 prevent fluid from flowing in the opposite direction.

A second position is when the stops 186 are about halfway down on the gap in the rotor housing 182. The second position is a manifold flush position where saline may be drawn into the manifold 150 to flush the bores and/or the pressure/suction device attached at the syringe port 160. The fluid path for the flush position is reversible, and so is only explained in one direction. With suction applied, fluid (saline) flows from the saline/waste port 156, passes through the saline/waste bore 168 to the saline/waste branch 174 to the saline/waste opening 192, into the second hole 232 through the first bore 216 in the rotary actuator 184 to the sixth hole 242 to the housing channel 243 to the syringe channel 252, through hole 250 and out to the syringe port 160. As neither check valve 200, 202 is in the fluid path, the fluid path may be reversed by applying pressure at the syringe port. When reversed, fluid flows back out through the saline/waste port 156 to the dual check valve/waste collection valve apparatus, if such is provided. It should be noted throughout this disclosure that separate saline and waste ports may be provided if a dual-check valve saline/waste apparatus is not used.

A third position is defined when the stops 186 are as far down as they can be within the rotor housing 182. In this position, the second bore 218 in the rotary actuator 184 is aligned with the third hole 234 and seventh hole 244 of the rotor housing 182. This position allows for aspiration from the catheter port 152 to the syringe port 160. Again, neither check valve 200, 202 is in the fluid path, so the path is reversible. Fluid which is aspirated from a medical device attached to the catheter port 152 follows the following path: from a medical device into the catheter port, through the main bore 162 to the main bore opening 194, and the main bus 196 into the bore-side channel 235 to the third opening 234, through the second bore 218 and seventh hole 244 to the housing channel 243, to the syringe channel, through hole 250 and out through the syringe port 160.

A fourth configuration may also be defined, this configuration not necessarily requiring any particular position for the rotary actuator 184. In the fourth configuration, the stopcock 170 may be turned so that the saline/waste bore 168 is coupled only to the pressurized saline bore 172.

Though not shown, a fifth configuration may also be defined in a further embodiment. In the further embodiment, additional check valves would be included in the rotary actuator 184. The check valves would be provided to align with second holes 232, 242 and the fourth holes 236, 246. The check valves would be disposed such that fluid could flow only from the saline/waste port 156, through the saline waste bore, to the syringe port via the second holes 232, 242 and the check valve in the rotary actuator 184, and then from the syringe port via the fourth holes 236, 246 to the main bore 162 and out to the catheter port. The fifth configuration would require placing the rotary actuator at a fourth position between the second and third positions.

Figure 17:
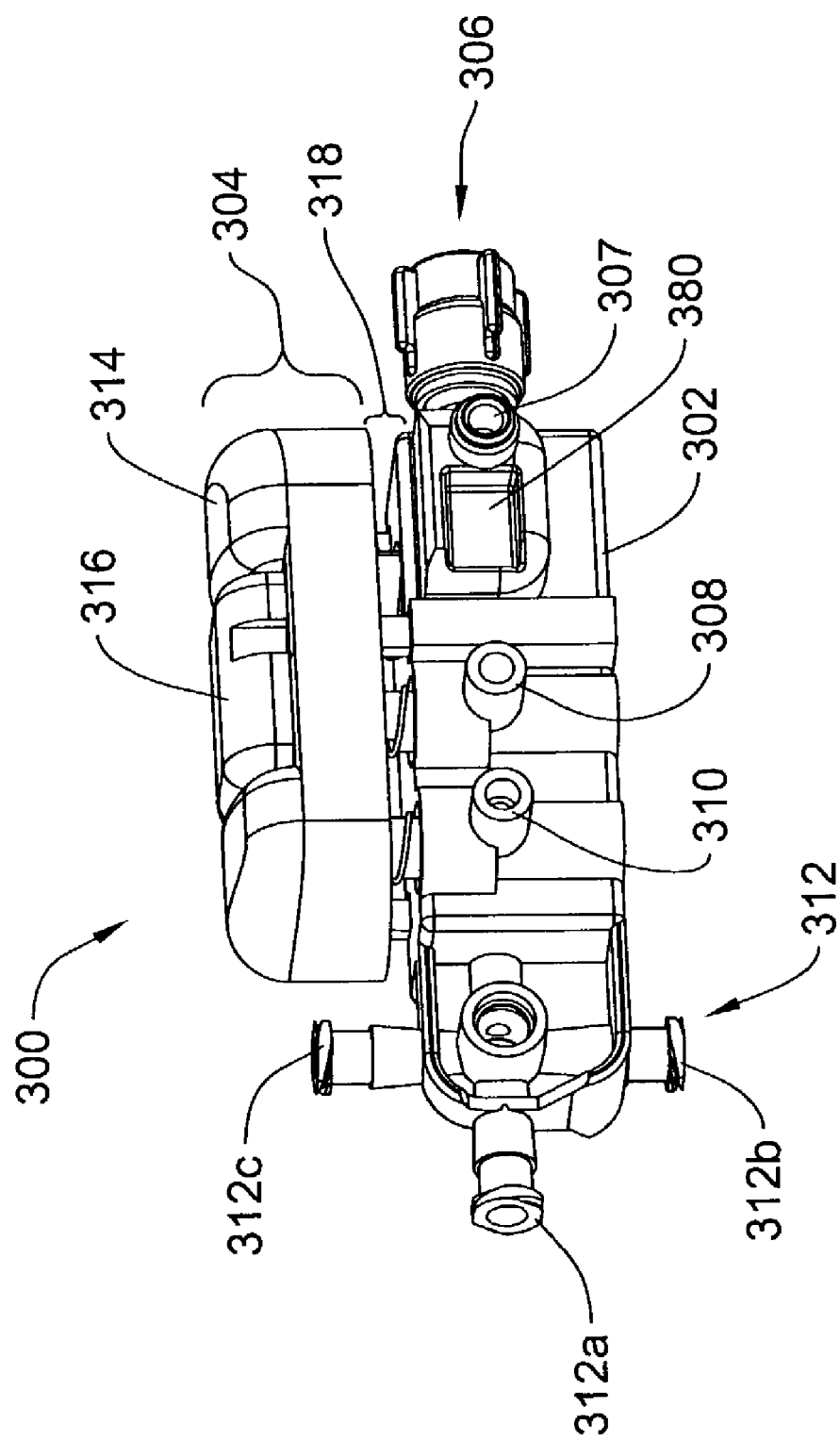
FIG. 17 is a perspective view of a fifth illustrative embodiment using a pushbutton scheme to control manifold valves.

FIG. 17 is a perspective view of a fifth illustrative embodiment using a pushbutton scheme to control manifold valves. The manifold 300 includes a port housing 302 and a button actuator 304. The port housing 302 includes a catheter port 306, an auxiliary port 307, a saline/waste port 308, a contrast port 310, and three syringe ports 312a, 312b, 312c which, for the purposes of explanation herein, will be described as a single syringe port 312 unless otherwise noted. In one illustrative embodiment, the manifold 300 may have a pressure/suction port 312a, a medication port 312b, and a pressurized saline port 312c, though any other configuration or placement may be used. The button actuator 304 includes an outer button 314 and an inner button 316.

The manifold 300 is illustrated "at rest" or in what may be described as its default position. When the outer button 314 is depressed, the gap 318 illustrated is closed so the outer button rests against the port housing 302. Depressing the outer button brings the inner button 316 down as well, however, the inner button 316 does not rest against the port housing 302 until the inner button 316 is itself further depressed.

Figure 18:
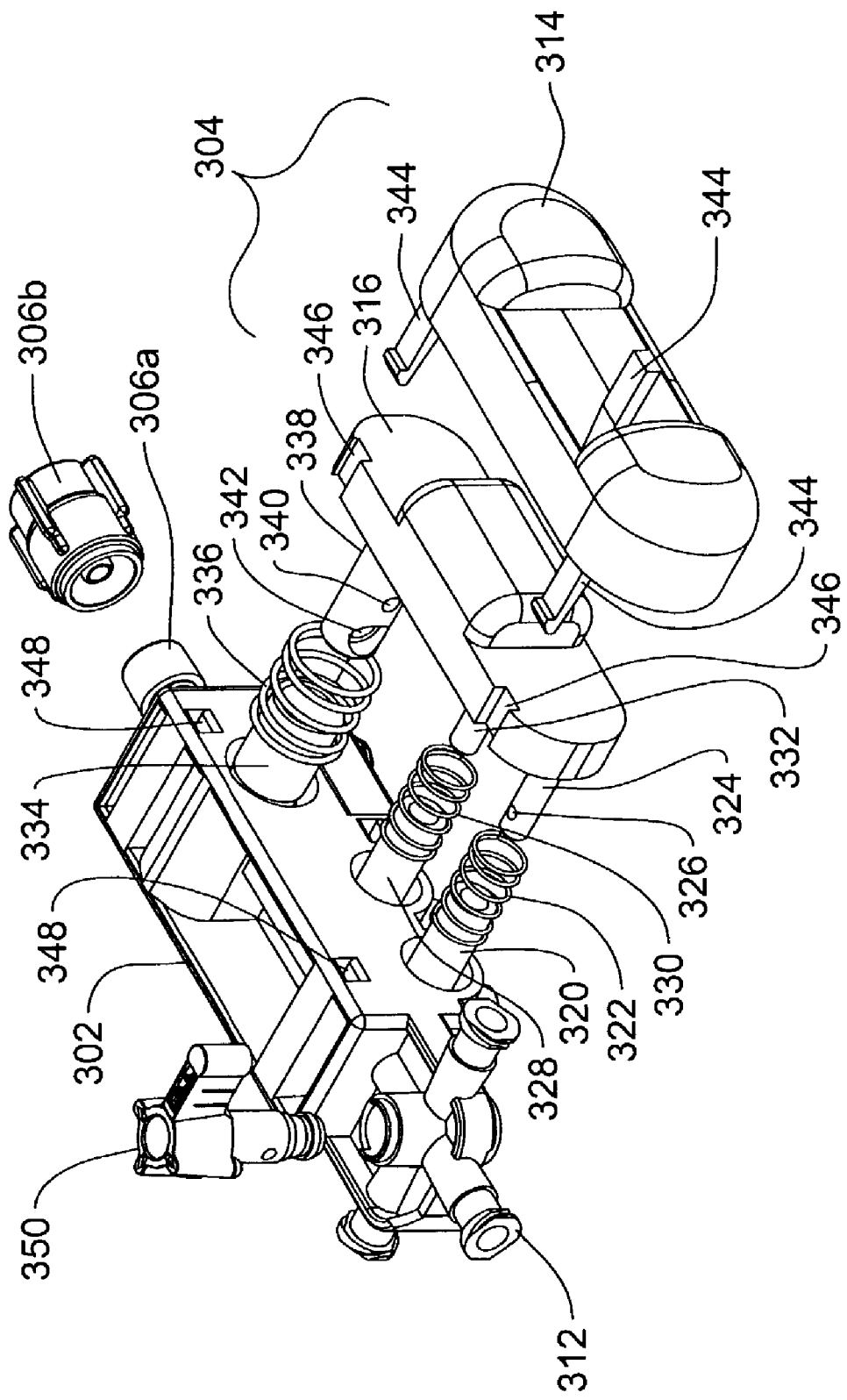
FIG. 18 is an exploded view of the illustrative embodiment of FIG. 17.

FIG. 18 is an exploded view of the illustrative embodiment of FIG. 17, illustrating in greater detail the parts of the manifold 300. The catheter port 306a, 306b is illustrated in the form of a port 306a and rotating adaptor 306b that allows rotation of the manifold relative to the catheter. This is a feature that may be included in some embodiments, while other adaptors and ports may also be used. Also notable is a stopcock 350 which allows for selection between the several couplings at the syringe port 312.

Greater detail is also shown in FIG. 18 with respect to the valve shafts attached to the button mechanism 304. In particular, the middle button 316 is coupled to a contrast valve shaft 324 having a first side opening 326. The contrast valve shaft 324 is aligned with a contrast valve receiver 320 on the port housing 302, with a first spring 322 therebetween. The middle button 316 is also coupled to a saline/waste valve shaft 332 having a side opening which is blocked in the perspective view of FIG. 18, the saline/waste valve shaft 332 being aligned with a saline/waste valve receiver 328 again having a second spring 330 therebetween. Finally, the middle button 316 includes a main valve shaft 338 adapted for insertion to a main valve receiver 334 with a third spring 336 therebetween, the main valve shaft 338 including a valve bore 340 therethrough and a check valve seat 342 therein. The relative alignment of the side openings 326, 332 and the valve bore 340 and check valve seat 342 is explained in more detail by reference to FIG. 19.

Also illustrated are clips 344 which are used to couple the outer button 314 to the port housing 302 by insertion through grooves 346 in the inner button 316 and into the slots 348 in the port housing 302. The clips 344 may be of a size such that the springs 322, 330, 336 are under a small amount of compression when the manifold is "at rest" as shown in FIG. 17. This sizing assures that the inner and outer buttons 314, 316, when not depressed, will return to their default location so that the contrast injection stage, which is supposed to occur when neither button 314, 316 is depressed, does indeed occur.

Figure 19:
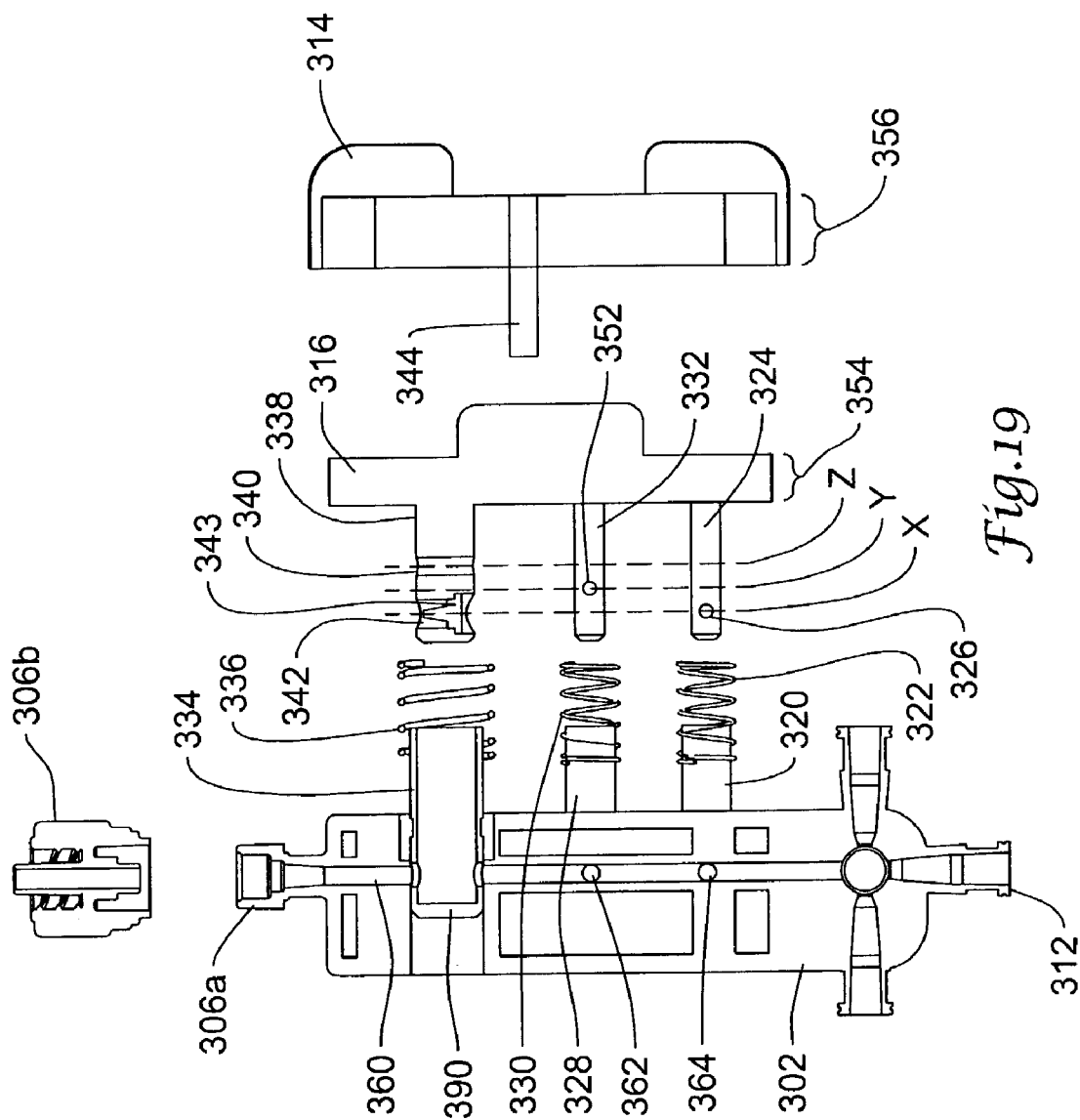
FIG. 19 is a cross-sectional view corresponding to the exploded view of FIG. 18.

FIG. 19 is a cross-sectional exploded view corresponding to the illustrative embodiment of FIG. 17. The relative sizes of the outer button 314 and the inner button 316 are illustrated. It should be noted that the outer button 314 has an outer collar depth 356 that is greater than the thickness 354 of the inner button 316, such that when the outer button 314 is fully depressed and contacts the port housing 302, the inner button 316 is not fully depressed. A feature blocked in the view of FIG. 18 is the saline/waste side opening 352 in the saline/waste valve shaft 332. The auxiliary port 307 shown in FIG. 17.

Additional details of the port housing 302 may now be explained. In particular, the port housing 302 includes a main bore 360 running the length thereof, and including a saline/waste side port 362 and a contrast side port 364. Lines X, Y, and Z are included and shown in alignment with the valve shafts 324, 332, 338 to aid in understanding three different positions which the buttons 304 and port housing 302 can adopt. The check valve seat 342 is shown with a check valve 343 inserted. The side ports 362, 364 are both placed to reach from the internal bores of the saline/waste and contrast valve receivers 320, 328 to the main bore 360.

The operation of the overall manifold 300 may now be explained in several stages. In a first, "rest" or default position where neither button 314, 316 is depressed, the device, when assembled, has line X even with the main bore 360. This means that the contrast valve opening 326 aligns with the contrast side port 364, creating fluid communication between the contrast port 310 and the main bore 360. Also, the check valve 343 in the main valve shaft 338 would lie in line with the main bore 360. As such, when suction is applied at the syringe port 312, contrast fluid flows into the main bore 360, and when pressure is applied at the syringe port 312, fluid flows from the main bore 360 out through the catheter port 306. The contrast port 310 or the contrast media source attached to the contrast port 310 may include an additional check valve to prevent fluid backflow to the contrast port 310. The inclusion of the check valve 343 in line with the main valve shaft 338 prevents fluid from being sucked in through the catheter port 306 while the manifold 300 is in its default or "rest" position.

With the outer button 314 depressed, the depth 356 causes the outer button 314 to come to rest when line Y is aligned with the main bore 360. As such, the main bore 360 would be clocked at the main valve shaft 338 because there is no opening corresponding to line Y on the main valve shaft 338. This blocks the catheter port 306 from suction and/or pressure. The contrast valve shaft 324 does not include an opening, but the saline/waste valve shaft 332 includes a saline/waste valve opening 352. The saline/waste valve opening 352 couples to the saline/waste side port 362. When suction is applied with this configuration, saline is pulled into the main bore 360 through the saline/waste valve opening 352, and then passes through the syringe port 312 to a pressure/suction device attached there. If pressure is applied, fluid passes in through the syringe port 312 through the main bore 360 and out through saline/waste side port 362 to the saline/waste valve opening 352 and out to a waste receptacle attached to the saline/waste port 308.

A third configuration is defined when the inner button 316 is depressed. Because the inner button 316 is not as thick 354 as the depth 356 of the outer button 314, the inner button may be depressed even further than when it is held down by the outer button 314. With the inner button 316 fully depressed, line Z aligns with the main bore 360. Because neither valve shaft 324, 332 has an opening corresponding to line Z, neither contrast fluid nor saline passes into the main bore 360, and waste is not disposed of, either. However, the main valve shaft 338 includes an opening 340 therethrough, which means that this third configuration allows fluid to flow through the main bore 360. Thus, this third configuration is used to aspirate fluid from the catheter port 306 into the main bore 360 when suction is applied at the syringe port 312. Because there is no check valve in the opening 340, fluid may also be passed into a medical device attached at the catheter port 306. This may allow for medicine to be infused. Though not shown in FIG. 19, the auxiliary port 307 shown in FIG. 17 may couple to the main bore 360 between the catheter port 306 and the main valve receiver 334, though the exact location of the auxiliary port 307 on the port housing 302 and its coupling to the main bore 360 may be varied widely.

Two additional features of the embodiment of FIGS. 17–19 should also be noted. FIG. 17 illustrates a manifold mounted transducer 380 which may be included as a build-in member for measuring pressure. By building the transducer 380 into the manifold 300, better measurements may be achieved by placing the actual transducing mechanism directly in the flow path of the manifold itself 300, rather than relying on a transducer which is attached via tubing or other fluid conduit, since such tubing and/or conduit can introduce mismeasurement errors and possible contaminants to the system. Further, including an integrated transducer may simplify the process of setting up the manifold 300.

Referring now to FIG. 19, it should also be noted that sleeve 390 is also illustrated. The sleeve 390 may be an elastomeric piece used to perform a sealing function on any of the valve shaft 324, 332, 338. While in some embodiments, a friction fit seal will be used around each valve shaft 324, 332, 338 to provide fluid sealing within the manifold 300, in other embodiments an elastomeric sleeve may be included attached either to the valve shaft 324, 332, 338 or placed within the housing 302. In a further embodiment, the sleeve 390 may include open channels or gaps for allowing fluid flow, such that, with the sleeve 390 attached to a valve shaft 324, 332, 338, fluid could flow around the valve shaft 324, 332, 338 rather than through a bore defined in the valve shaft itself 324, 332, 338. In the further embodiment (not shown), the holes 326, 340, 352 could be excluded from the valve shaft 324, 332, 338, with the fluid flow function provided by an elastomeric sleeve 390.

Figure 20:
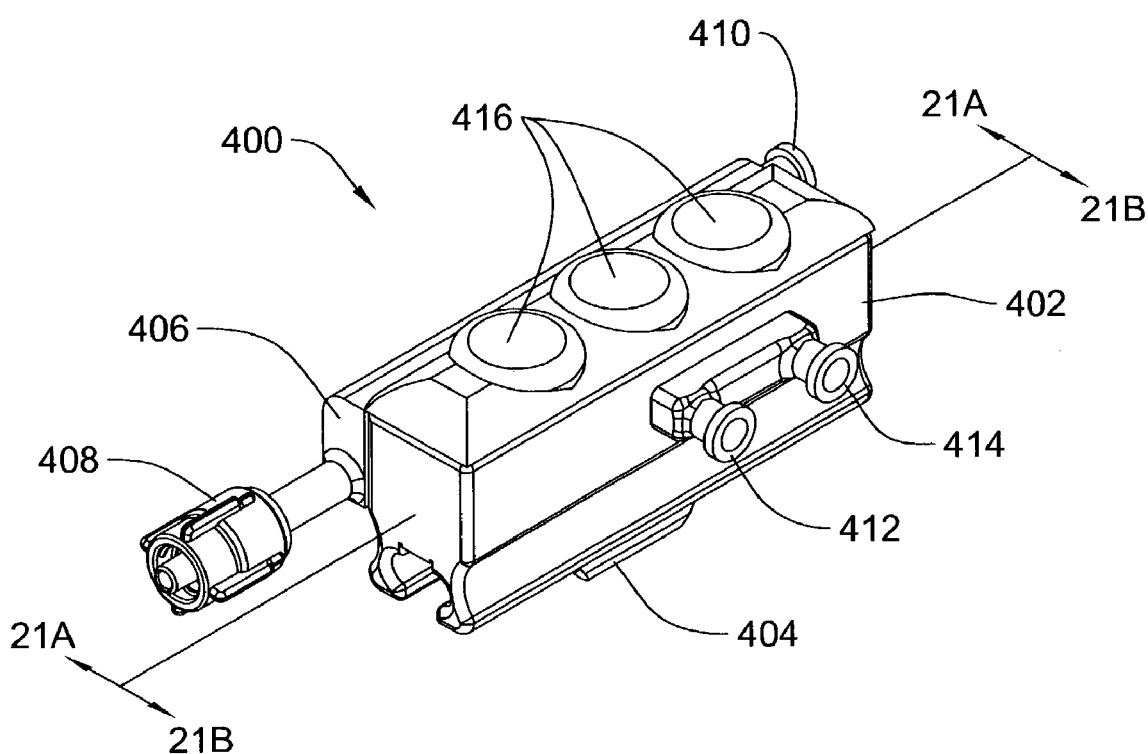
FIG. 20 is a perspective view of another illustrative embodiment including a sliding actuator for controlling valves.

FIG. 20 is a perspective view of another illustrative embodiment including a sliding mechanism to depress a selected button. The manifold 400 includes a main housing 402, a sliding actuator 404, and a side housing 406. The side housing 406 is coupled to a catheter port 408 at one end and a syringe port 410 at the other end. The main housing 402 includes a saline/waste port 412 and a contrast port 414. The main housing 402 includes three chambers which are provided with chamber lids 416 that provide a fluid seal to each chamber as well as providing a resistance base for springs loading within each chamber, as is further explained below.

Figure 21A:
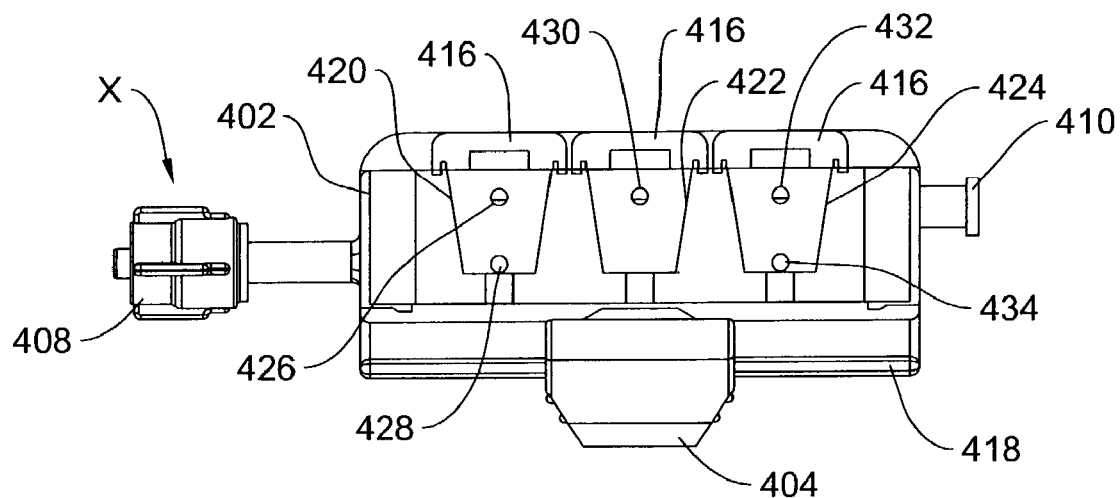
FIGS. 21A–21B are cross sectional views of the illustrative embodiment of FIG. 20 with certain parts excluded.
Figure 21B:
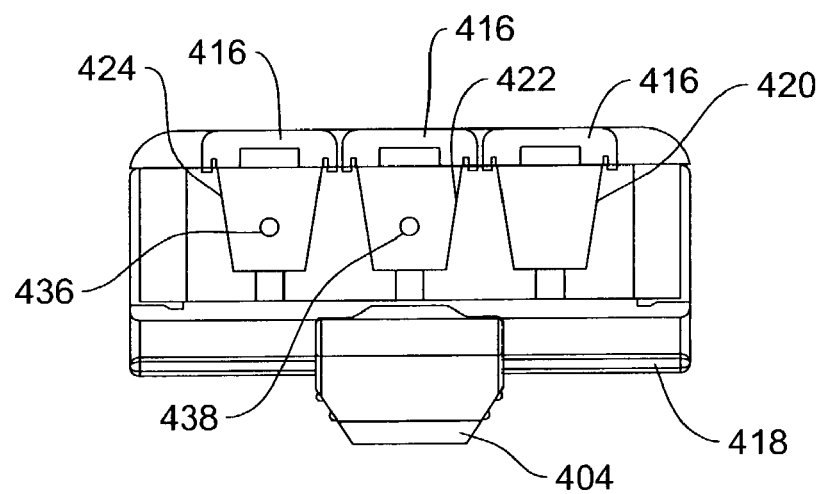

FIGS. 21A–21B are cross-sectional views of the illustrative embodiment of FIG. 20 with certain parts excluded. FIG. 21A is a cross section taken along line A—A in FIG. 20, facing toward the side housing. It can be seen that the slider 404 is disposed within a channel 418 which allows access to and limits the movement of the slider 404. A first chamber 420, a second chamber 422, and a third chamber 424 are illustrated within the main housing 402. The first chamber 420 includes openings to a first bore 426 and a second bore 428. The second chamber 422 includes an opening to a third bore 430, and the third chamber 424 includes openings to a fourth bore 432 and a fifth bore 434. The first, third and fourth bores 426, 430, 432 are all aligned in a row that is level with the syringe port 410, while the second and fifth bores 428, 434 are aligned in a row parallel to the row formed by the other three bores 426, 430, 432 and which is aligned with the catheter port 408.

FIG. 21B is a cross section taken along line B—B in FIG. 20, facing the opposite direction from the cross section of FIG. 21A. Note that, because the cross section faces the opposite direction, the chambers are reversed, so the third chamber 424 is now on the left and the first chamber 420 is on the right. Facing this direction, the third chamber 424 includes an opening to a contrast bore 436, and the second chamber includes an opening to a saline/waste bore 438. The contrast bore 436 is coupled to the contrast port 412 illustrated in FIG. 20, and may include a one-way check valve if so desired. The saline/waste bore 438 is coupled to the saline/waste port 414 illustrated in FIG. 20.

Figure 22A:
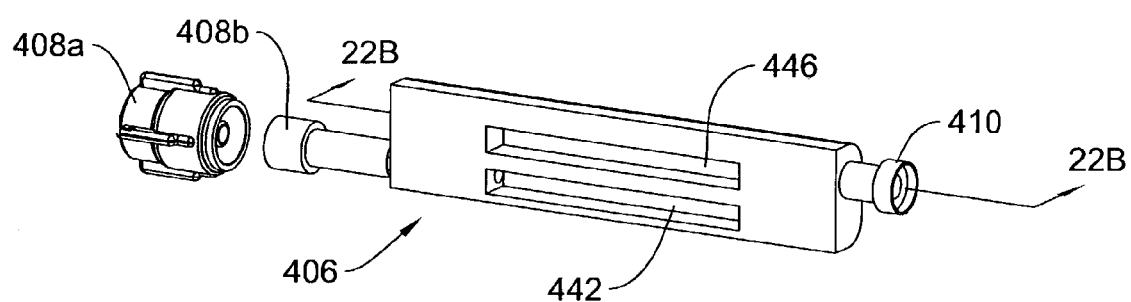
FIGS. 22A–22B are a cross sectional view and a perspective view, respectively, of the coupler housing of FIG. 20.
Figure 22B:
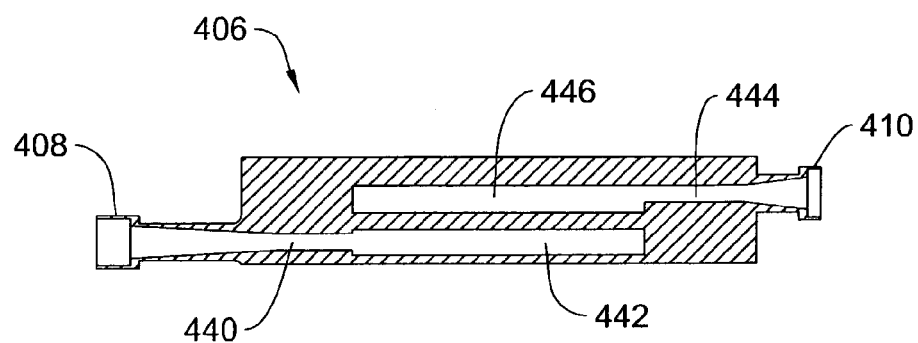

FIGS. 22A–22B are a perspective view and a cross-sectional view, respectively, of the side housing of FIG. 20. The catheter port 408 is illustrated in the form of a port 408*a* and rotating adaptor 408*b* that allows rotation of the manifold relative to the catheter. This is a feature that may be included in some embodiments, while other adaptors and ports may also be used. The side housing includes a catheter channel 442 which is coupled to the catheter port 408*a*, 408*b*, and a syringe channel 446 which is coupled to the syringe port 410. The channels 442, 446 are provided at locations which align with several of the bores shown in FIG. 21A so that the bores provide fluid communication between the three chambers and the side housing 406. In particular, the catheter channel 442 aligns with the second bore 428 and the fifth bore 434. The syringe channel 446 aligns with the first bore 426, the third bore 430, and the fourth bore 432.

FIG. 22B illustrates a cross-sectional view corresponding to line B—B of FIG. 22A. The cross section illustrates that the catheter port 408 is coupled to the catheter channel 442 by a catheter bore 440, and that the syringe port 410 is coupled to the syringe channel 446 by a syringe bore 444. The channels 442, 446 do not fluidly communicate with one another except as controlled by the chambers and the slider actuator, as further explained below after additional elements of the illustrative example are introduced.

Figure 23:
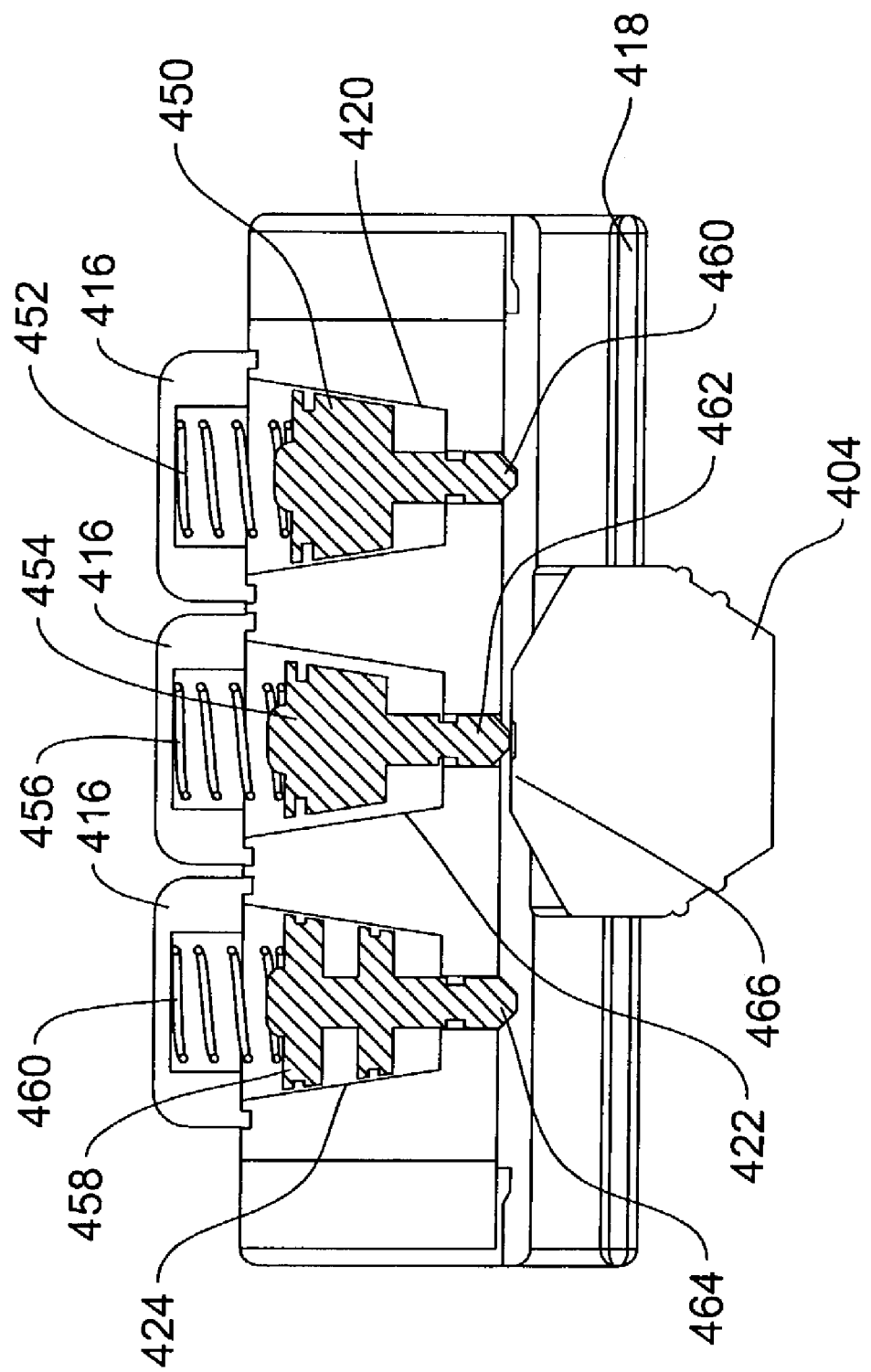
FIG. 23 is another cross sectional illustration of the illustrative embodiment of FIG. 20 with several additional parts included to illustrate a slider actuation mechanism.

FIG. 23 is another cross-sectional illustration of the illustrative embodiment of FIG. 20 with several additional parts included to illustrate a slider actuation mechanism. The view of FIG. 23 corresponds to the cross-sectional view of FIG. 21B, so again, the first chamber 420 is on the right while the third chamber 424 is on the left. The first chamber 420 is now shown as including a first plunger 450 and a first spring 452. The second chamber 422 includes a second plunger 454 and second spring 456, and the third chamber 424 includes a third plunger 458 and a third spring 460. The springs 452, 456, 460 are provided to bias the plungers 450, 454, 458 against the sides of their respective chambers 420, 422, 424. When so biased, the plungers 450, 454, 458 block fluid communication between the chambers 420, 422, 424 and several of the bores 426, 428, 430, 432, 434, 436, 438.

The mechanism for opening selected bores to fluid communication for the illustrative embodiment includes use of the slider 404. The following explanations of three illustrative positions require reference to multiple Figures at the same time.

A first position is a contrast infusion position. When in the first position, the slider 404 is placed such that the edge 466 engages the third plunger tip 464, moving the third plunger 458 against the spring 460 and away from the walls of the third chamber 424. With the third plunger 458 away from the walls of the third chamber 424, the first and second bores 426, 428 and the contrast bore 436 are free to conduct fluid. When suction is applied at the syringe port 410, contrast fluid or other media is sucked through the contrast port 414, through the contrast bore 436, into the third chamber 424, through the fourth bore 432 to the syringe channel 446, through the syringe bore 444, and out to the syringe port 410. When pressure is applied at the syringe port 410, fluid is forced through the syringe port 410, through the syringe bore 444 into the syringe channel 446, through the fourth bore 432 and into the third chamber 424. Because either the contrast source coupled to the contrast port 414, the contrast bore 436, or the contrast port itself will include a check valve, once the fluid is forced into the third chamber 424 from the syringe channel 446, the fluid must exit through the fifth channel 434 into the catheter channel 442, to catheter bore 440 and out to the catheter port 408.

For the second position, which is a manifold flush position, the slider 404 is placed as shown in FIG. 23 such that the edge 466 engages the second plunger tip 462, pushing the second plunger 454 away from the walls of the second chamber 422. With the second plunger 454 away from the walls of the second chamber 422, the openings to the saline/waste bore 438 (FIG. 21B) and the third bore 430 are unblocked. When suction is applied at the syringe port 410, saline is pulled into the manifold 400 at the saline/waste port 412, through the saline/waste bore 438, into the second chamber 422, through the third bore 430, into the syringe channel 446, through the syringe bore 444 and out through the syringe port 410. When pressure is applied at the syringe port 410, fluid is forced into the manifold 400 through the syringe port 410, into the syringe bore 444 to the syringe channel 446, through the third bore 430 into the second chamber 422, out to the saline/waste bore 438, to the saline/waste port 412 and into a waste receptacle attached thereto.

A third position is provided to allow aspiration of fluid from a medical device coupled to the catheter port 408. The third position is defined when the slider 404 is placed over the first chamber 420 such that the edge 466 engages the first plunger tip 460 and forces the first plunger 450 away from the walls of the first chamber 420. This opens the first and second bores 426, 428 to fluid conveyance. Because the only openings in the first chamber 420 are to the first channel 426 and the second channel 428, there is only one available fluid path. When suction is applied at the syringe port 410, fluid is pulled from the catheter port 408 into the catheter bore 440, to the catheter channel 442, through the second bore 428 into the first chamber 420, through the first bore 426 to the syringe channel 446 to the syringe bore 444, and out to the syringe port 410. When pressure is applied at the syringe port, the reverse fluid path may be followed. If so desired, a check valve may be placed in the first bore 426 or the second bore 428 to prevent fluid flow into the catheter port 408 if fluid is to be aspirated and disposed.

For each of the several illustrative embodiments above, various additional features including additional ports, check valves, and actuator positions may be provided. The above illustrative embodiments are relatively simple, yet effective, mechanisms for improving the efficiency and speed of a number of medical procedures. The exact materials and methods of attachment, as well as the illustrative sources and receptacles (saline, waste, contrast, pressurized saline, syringes, and catheters) are provided for illustrative purposes and should not be understood to limit the invention to these particular elements.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A manifold for coupling a pressure/suction source and a plurality of diagnostic or therapeutic substance sources to a medical device adapted for use of the diagnostic or therapeutic substances, the manifold comprising:

a housing including a plurality of ports including a first port, the first port in fluid communication with a bifurcated bore including a first branch and a second branch, wherein the first branch of the bifurcated bore includes a check valve; and valve means having a first position, a second position, and a third position, wherein the first position is adapted for infusing a first substance to the medical device, the second position is adapted for flushing the manifold, and the third position is adapted for draining fluid from the medical device.

2. The manifold of claim 1, wherein the valve means is coupled to selector means allowing a user to select one of the first position, the second position, and the third position, the selector means comprising a mechanism allowing the user to select one of the positions by manipulating a single element.

3. The manifold of claim 2, wherein the mechanism is a plurality of buttons, wherein depressing a button selects a position.

4. The manifold of claim 3, wherein the buttons are interconnected such that depressing a first button causes a second button to release from a depressed position.

5. The manifold of claim 2, wherein the mechanism is a rotatable member, wherein rotation of the rotatable member selects a position.

6. The manifold of claim 2, wherein ibe mechanism is a sliding member, wherein sliding of the sliding member selects a position.

7. The manifold of claim 1, further comprising indicating means for indicating whether the valve means is in a selected position.

8. The manifold of claim 1, wherein the second branch of the bifurcated bore is without a check valve.

9. A manifold for controlling which of several ports is coupled to a medical device, the manifold comprising:
- a port for coupling to a pressure/suction device;
- a port for coupling to a diagnostic or therapeutic substance source;
- a port for coupling to a saline/waste line;
- a port for coupling to the medical device; and
- a main valve including a rotating actuator having a number of bores therethrough and a housing providing a number of bores between the ports and the rotating actuator;
- wherein the rotating actuator and the bores selectively provide:
- a first fluid path coupling the pressure/suction port to the substance source port and the medical device port when the rotating actuator is in a first position for infusing the substance into the medical device, wherein the first fluid path further includes a first check valve for preventing aspiration from the medical device;
- a second fluid path coupling the pressure/suction port to the saline/waste line port when the rotating actuator is in a second position for flushing the manifold and pressure/suction device; and
- a third fluid path coupling the pressure/suction part to the medical device port when the rotating actuator is in a third position for aspirating fluid from the medical device, wherein the third fluid path includes the first check valve and wherein the rotating actuator is moved from the first position to the third position such that the first check valve, when in the third fluid path, operates to prevent injection of fluid to the medical device.

10. The manifold of claim 9, further comprising a valved bore for selectively coupling the saline/waste port to the medical device port.

11. The manifold of claim 9, further comprising a one-way valve placed in the fluid path between the substance port and the rotating actuator for preventing fluid flow from the rotating actuator back into the substance source.

12. The manifold of claim 9, wherein the substance is a contrast medium.

13. The manifold of claim 9, wherein the pressure/suction port is adapted to couple to a syringe.

14. The manifold of claim 9, wherein the medical device port is adapted to couple to a catheter.

15. The manifold of claim 9, wherein the first fluid path further includes a second check valve for preventing infusion of fluid to the substance source.

16. The manifold of claim 9, wherein the rotating actuator and the bores selectively provide a fourth fluid path coupling the saline/waste port to the medical device port.

17. The manifold of claim 9, further comprising a selector attached to the rotating aemator, the selector allowing a user to rotate the rotating actuator, the selector further including means for indicating the position of the rotating actuator.

18. A manifold for selectively controlling fluid communication of several ports with a medical device, the manifold comprising:
- a housing having a plurality of ports and a plurality of bores, wherein a first port is in fluid communication with a first bore, a second port is in fluid communication with a second bore, and a third port is in fluid communication with a bifurcated third bore, wherein a first branch of the bifurcated third bore includes a check valve and a second branch of the bifurcated third bore is without a check valve; and
- an actuatable valve for selectively controlling fluid communication among the plurality of bores.

19. The manifold of claim 18, further comprising a fourth port in fluid communication with a bifurcated fourth bore, wherein a first branch of the bifurcated fourth bore includes a check valve.

20. A manifold for selectively controlling fluid communication of several ports with a medical device, the manifold comprising:
- a housing having a plurality of ports, a plurality of bores, and a stopcock selectively segregating one or more of the plurality of ports of the housing; and
- an actuatable valve having a plurality of bores including a first bore, a second bore and a third bore, wherein each of the bores of the valve is in fluid communication with the remainder of the bores of the valve;
- wherein the valve is actuatable such that the plurality of bores of the valve are selectively aligned with the plurality of bores of the housing.

21. The manifold of claim 20, further comprising a selector handle connected to the valve for selectively actuating the valve.

22. The manifold of claim 21, wherein the selector handle rotatably actuates the valve.

23. The manifold of claim 21, wherein the housing further includes a check valve.

24. The manifold of claim 20, wherein the second bore of the valve includes a vertical groove.

25. The manifold of claim 20, wherein the valve further includes a fourth bore in fluid communication with the first, second and third bores.

* * * * *

UNITED STATES PATENT AND TRADEMARK OFFICE
CERTIFICATE OF CORRECTION

PATENT NO. : 7,172,572 B2
APPLICATION NO. : 10/375658
DATED : February 6, 2007
INVENTOR(S) : Scott A. Diamond et al.

It is certified that error appears in the above-identified patent and that said Letters Patent is hereby corrected as shown below:

Column 20
Line 65, delete "ibe" and insert therefor -- the --.

Column 21
Line 29, delete "part" and insert therefor -- port --.

Column 22
Line 5, delete "aemator" and insert therefor -- actuator --.

Signed and Sealed this

Twenty-second Day of May, 2007

JON W. DUDAS
*Director of the United States Patent and Trademark Office*